US012758170B2

(12) United States Patent
Chen et al.

(10) Patent No.: US 12,758,170 B2
(45) Date of Patent: Oct. 13, 2026

(54) SCANNING CABINS, METHODS FOR IDENTIFYING SCANNING CABINS, AND IMAGING SYSTEMS

(71) Applicant: WUHAN UNITED IMAGING LIFE SCIENCE INSTRUMENT CO., LTD., Wuhan (CN)

(72) Inventors: Jun Chen, Wuhan (CN); Tao Hong, Wuhan (CN); Hongxia Lei, Wuhan (CN)

(73) Assignee: WUHAN UNITED IMAGING LIFE SCIENCE INSTRUMENT CO., LTD., Wuhan (CN)

( * ) Notice: Subject to any disclaimer, the term of this patent is extended or adjusted under 35 U.S.C. 154(b) by 161 days.

(21) Appl. No.: 18/672,055

(22) Filed: May 23, 2024

(65) Prior Publication Data

US 2024/0307013 A1 Sep. 19, 2024

Related U.S. Application Data

(63) Continuation of application No. PCT/CN2022/102032, filed on Jun. 28, 2022.

(30) Foreign Application Priority Data

Nov. 26, 2021 (CN) ......................... 202122977655.2
Dec. 13, 2021 (CN) ......................... 202111517568.7
(Continued)

(51) Int. Cl.
*A61B 6/00* (2024.01)
*A61B 6/03* (2006.01)
*A61B 6/04* (2006.01)

(52) U.S. Cl.
CPC .............. *A61B 6/4494* (2013.01); *A61B 6/03* (2013.01); *A61B 6/045* (2013.01); *A61B 6/4411* (2013.01);
(Continued)

(58) Field of Classification Search
None
See application file for complete search history.

(56) References Cited

U.S. PATENT DOCUMENTS 4,644,467 A 2/1987 McCarthy
7,294,112 B1 11/2007 Dunlop
(Continued)

FOREIGN PATENT DOCUMENTS

CN 102658666 A 9/2012
CN 103735251 A 4/2014
(Continued)

OTHER PUBLICATIONS

First Office Action in Chinese Application No. 202111517568.7 mailed on Jun. 28, 2025, 14 pages.
(Continued)

*Primary Examiner* — Marcus H Taningco
(74) *Attorney, Agent, or Firm* — METIS IP LLC

(57) ABSTRACT

Embodiments of the present disclosure provide a scanning cabin, a method implemented on a computing device including a storage device and at least one processor for identifying the scanning cabin, and an imaging system. The method for identifying the scanning cabin may include obtaining coding information of the scanning cabin and determining a specification parameter of the scanning cabin based on the coding information and preset coding information. The method for identifying the scanning cabin provided by the embodiments of the present disclosure can accurately identify the scanning cabin in animal imaging, reduce the identification cost of the scanning cabin, and improve the identification efficiency of the scanning cabin.

20 Claims, 13 Drawing Sheets

(30) Foreign Application Priority Data

| | | | |
|---|---|---|---|
| Dec. 13, 2021 | (CN) | ......................... | 202123122869.8 |
| Dec. 15, 2021 | (CN) | ......................... | 202111535331.1 |

(52) U.S. Cl.
CPC ... *A61B 2503/40* (2013.01); *A61B 2560/0406* (2013.01); *A61B 2560/045* (2013.01); *A61B 2560/0468* (2013.01); *A61B 2562/0214* (2013.01); *A61B 2562/0271* (2013.01)

(56) References Cited

U.S. PATENT DOCUMENTS

| | | | | |
|---|---|---|---|---|
| 9,251,455 | B2 * | 2/2016 | Lin | G06K 19/0717 |
| 2005/0039699 | A1 | 2/2005 | Sato et al. | |
| 2008/0266115 | A1 | 10/2008 | Labrecque et al. | |
| 2009/0043172 | A1 | 2/2009 | Zagorchev et al. | |
| 2010/0076330 | A1 | 3/2010 | Kimura et al. | |
| 2010/0198047 | A1 | 8/2010 | Zagorchev et al. | |
| 2012/0294493 | A1 | 11/2012 | Kim et al. | |
| 2014/0277695 | A1 * | 9/2014 | Iqbal | B01L 9/06 700/225 |
| 2016/0287129 | A1 | 10/2016 | Atallah et al. | |
| 2017/0203118 | A1 | 7/2017 | Chang | |
| 2019/0000407 | A1 | 1/2019 | Muller et al. | |
| 2023/0011644 | A1 * | 1/2023 | Zhao | A61B 6/5282 |

FOREIGN PATENT DOCUMENTS

| | | | |
|---|---|---|---|
| CN | 106264593 | A | 1/2017 |
| CN | 106529196 | A | 3/2017 |
| CN | 107348960 | A | 11/2017 |
| CN | 109461228 | A | 3/2019 |
| CN | 109646146 | A | 4/2019 |
| CN | 110742639 | A | 2/2020 |
| CN | 111195126 | A | 5/2020 |
| CN | 111767846 | A | 10/2020 |
| CN | 112274274 | A | 1/2021 |
| CN | 212624284 | U | 2/2021 |
| CN | 113125471 | A | 7/2021 |
| CN | 116262044 | A | 6/2023 |
| GB | 857862 | A | 1/1961 |

OTHER PUBLICATIONS

First Office Action in Chinese Application No. 202111535331.1 mailed on Aug. 18, 2025, 18 pages.

International Search Report in PCT/CN2022/102032 mailed on Sep. 26, 2022, 8 pages.

Written Opinion in PCT/CN2022/102032 mailed on Sep. 26, 2022, 8 pages.

* cited by examiner

111

SCANNING CABINS, METHODS FOR IDENTIFYING SCANNING CABINS, AND IMAGING SYSTEMS

CROSS-REFERENCE TO RELATED APPLICATIONS

This application is a Continuation of International Application No. PCT/CN2022/102032, filed on Jun. 28, 2022, which claims priority of Chinese Patent Application No. 202122977655.2 filed on Nov. 26, 2021, Chinese Patent Application No. 202111517568.7 filed on Dec. 13, 2021, Chinese Patent Application No. 202123122869.8 filed on Dec. 13, 2021, Chinese Patent Application No. 202111535331.1 filed on Dec. 15, 2021, the contents of each of which are incorporated herein by reference.

TECHNICAL FIELD

The present disclosure relates to the field of life science instruments, and in particular, to scanning cabins, methods for identifying the scanning cabins, and imaging systems.

BACKGROUND

In vivo animal imaging (also referred to as animal scanning) technology uses imaging techniques to study biological processes at the tissue, cellular, and molecular levels under living conditions without harming animals. During animal imaging, it is generally necessary to place an animal inside a scanning cabin, which is then scanned by a corresponding scanning device. During a process of animal imaging, the scanning cabin needs to be used to monitor a physiological status (e.g., respiration, electrocardiogram, etc.) of the animal placed inside the scanning cabin. By reasonably configuring a structure of the scanning cabin, it is possible to simplify the structure of the scanning cabin while providing a suitable environment for the scanned animal, reducing a risk of interference to the scanned animal, improving the accuracy and efficiency of measuring physiological signals of the scanned animal, and facilitating the operation of an experimenter. In addition, since types and sizes of animals to be scanned may vary, it is necessary to replace, before scanning, scanning cabins having different specification parameters tailored to different scanning objects and scanning modalities. This process also involves the identification of the scanning cabin. Therefore, how to reduce the identification cost of the scanning cabin and improve the efficiency and accuracy of scanning cabin identification are currently noteworthy issues.

SUMMARY

One embodiment of the present disclosure provides a method implemented on a computing device including a storage device and at least one processor for identifying a scanning cabin (hereinafter referred to as the method for identifying the scanning cabin or the method). The method may include: obtaining coding information of the scanning cabin; and determining a specification parameter of the scanning cabin based on the coding information and preset coding information. In some embodiments, the determining a specification parameter of the scanning cabin based on the coding information and preset coding information may include: determining, from a plurality of pieces of the preset coding information, whether a piece of preset coding information corresponding to the coding information exists in a database, wherein each piece of the plurality of pieces of preset coding information corresponds to a specification parameter of a single scanning cabin; in response to a determination that the piece of preset coding information corresponding to the coding information exists in the database, obtaining the specification parameter of the scanning cabin corresponding to the piece of preset coding information from the database. In some embodiments, the method may further include determining one or more scanning parameters corresponding to the scanning cabin based on the specification parameter of the scanning cabin, wherein the one or more scanning parameters include a resolution threshold corresponding to the scanning cabin. In some embodiments, the method may further include: obtaining a resolution inputted through a terminal device, and determining whether the resolution is less than the resolution threshold of the scanning cabin, in response to a determination that the resolution is less than the resolution threshold, providing a prompt message to suggest re-entering the resolution or replacing the scanning cabin; or setting a value range of the resolution inputted through the terminal device based on the resolution threshold.

One embodiment of the present disclosure provides a scanning cabin, which may include a cabin for placing a scanning object and one or more functional components integrated in the cabin. The one or more functional components may include: an electrocardiogram detection device for electrocardiogram detection of the scanning object; a thermometer for monitoring a body temperature of the scanning object; and one or more temperature regulators for regulating a temperature of a region where the scanning object is located. Each of the one or more temperature regulators may include a heating pipeline.

One embodiment of the present disclosure provides an imaging system, which may include a scanning cabin, a scanning cabin support arm, and a controller. The scanning cabin may include a connector socket and a connector plug may be provided on the scanning cabin support arm. The connector socket may be configured to connect with the connector plug on the scanning cabin support arm, and the connector socket, when connected with the connector plug, may generate coding information for the scanning cabin. The controller may be configured to: determine whether a piece of preset coding information corresponding to the coding information exists in a database, and in response to a determination that the piece of preset coding information corresponding to the coding information exists in the database, obtain a specification parameter of the scanning cabin corresponding to the piece of preset coding information from the database.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
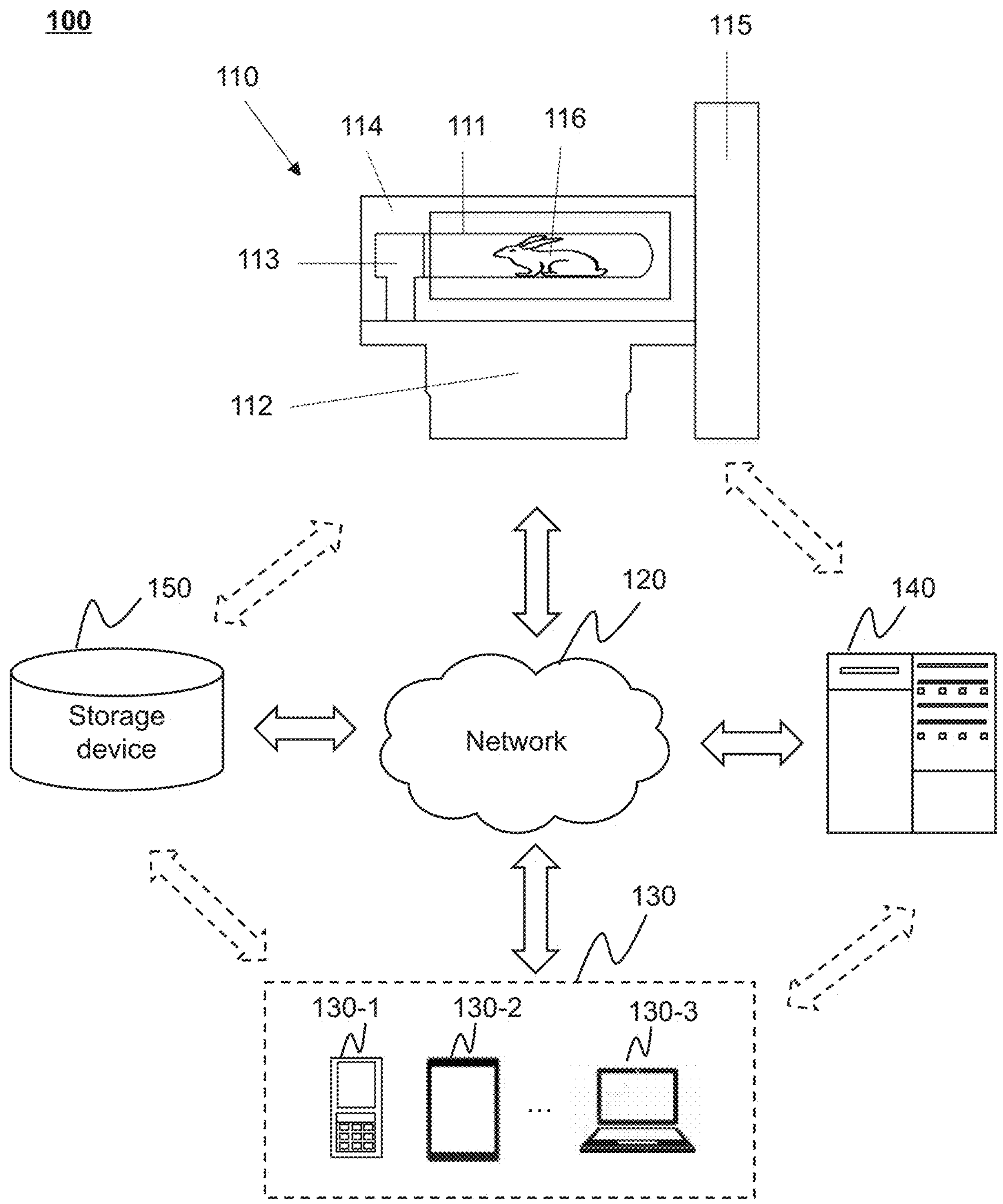
FIG. 1 is a schematic diagram of an application scenario of an imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

It should be understood that the terms “system,” “device,” “unit,” and/or “module” used herein are used to distinguish different levels of components, elements, parts, portions, or assemblies. However, if other words can achieve the same purpose, alternative expressions may be used to replace the aforementioned terms.

The terminology used herein is for the purpose of describing particular example embodiments only and is not intended to be limiting. As used herein, the singular forms “a,” “an,” and “the” may be intended to include the plural forms as well, unless the context clearly indicates otherwise. It will be further understood that the terms “comprise,” “comprises,” and/or “comprising,” “include,” “includes,” and/or “including,” when used in this disclosure, specify the presence of stated features, integers, steps, operations, elements, and/or components, but do not preclude the presence or addition of one or more other features, integers, steps, operations, elements, components, and/or groups thereof.

Flowcharts are used in the present disclosure to illustrate the operations performed by the system according to some embodiments of the present disclosure. It should be understood that the operations described herein are not necessarily executed in a specific order. Instead, they may be executed in reverse order or simultaneously. Additionally, other operations may be added to these processes or certain operation or operations may be removed.

During animal imaging, an animal to be scanned is placed inside a scanning cabin and scanned using a corresponding scanning device (e.g., a computed tomography (CT) device, a positron emission tomography (PET) device, a magnetic resonance imaging (MRI) device, etc.). During this process, measurements of the animal’s respiratory and electrocardiographic signals are generally taken.

In some embodiments, physiological monitoring of an animal undergoing imaging is conducted as contact-based physiological monitoring, wherein a physiological signal is measured by directly contacting a corresponding detection device with the animal to be scanned. Subsequently, the physiological signal is transmitted via a transmission cable to an outside of the scanning cabin. For example, when monitoring a body temperature of an animal, a rectal temperature sensor may be inserted into the animals’ rectum to measure the body temperature of the animal. As another example, when monitoring respiration of an animal, a respiratory pad may be placed on the animal’s abdomen, and a movement of the animals’ abdomen compresses gas within the respiratory pad to generate a respiratory signal. As yet another example, when monitoring electrocardiogram (ECG) of an animal, direct contact with the animal may be needed to acquire an electrode signal. In some embodiments, direct contact with the animal for electrode signal acquisition may be in an invasive manner and a non-invasive manner. In the invasive manner, an electrode needle may be inserted under a skin of the animal for electrode signal acquisition, and in the non-invasive manner, an electrode may be attached to the skin of the animal. Employing contact-based physiological monitoring to measure the physiological signals of the animal to be scanned typically requires a longer preparation time. During a preparation process, the animal to be scanned may awake from light anesthesia, thus imposing higher demands on the speed of operation for an experimenter. Moreover, direct contact between a detection device and the animal to be scanned is cumbersome and may interfere with the animals' anesthesia. Furthermore, due to variations in specification parameters of scanning cabins adapted for different types and sizes of animals, the scanning cabin in an imaging system for animal scanning is replaceable to enhance the convenience of the scanning process. However, adopting contact-based physiological monitoring may necessitate multiple connections of transmission cables used for transmitting physiological signals, which may lead to signal attenuation during the transmission process, thereby reducing the accuracy of signal measurements.

In practical operation, since the scanning cabins in the imaging system for animal scanning are replaceable, it is necessary to identify a scanning cabin before scanning to adapt the scanning cabin to the corresponding animal to be scanned. In some embodiments, relevant characteristic information (e.g., shape, identification, etc.) of the scanning cabin may be obtained manually to determine the corresponding scanning cabin. However, manual determination often leads to deviations and incorrect identification results. In some embodiments, the relevant characteristic information of the scanning cabin may be obtained through collected visual information, sensor information, or electronic tag information, and further, the corresponding scanning cabin may be determined based on the relevant characteristic information. For example, image features of the scanning cabin may be obtained and classified to obtain an identification result of the scanning cabin. As another example, the corresponding scanning cabin may be determined by communicating with electronic tags using radio frequency signals and a card reader to scan contents of the electronic tags. However, this method for identifying the scanning cabin generally requires complex sensor equipment, computing devices, and algorithms, resulting in high identification costs, low identification efficiency, and a risk of misjudgment.

Embodiments of the present disclosure provide a scanning cabin, a method for identifying the scanning cabin, and an imaging system. The scanning cabin provided in the embodiments of the present disclosure achieves non-contact physiological monitoring of the animal to be scanned by integrating one or more functional components (e.g., an electrocardiogram detection device, a camera device, a thermometer, etc.) in the cabin. That is, detection devices such as the electrocardiogram detection device, the camera device, the thermometer, etc., can measure physiological status signals (e.g., an electrocardiogram signal, a respiratory signal, a body temperature, etc.) of the animal to be scanned without direct contact. This not only shortens the preparation time, simplifies operation, and enhances experimental efficiency but also does not affect the anesthesia of the animal to be scanned. Additionally, the measured physiological status signals can be wirelessly transmitted to a computer end, reducing signal attenuation during transmission and avoiding multiple connections of transmission cables, thereby reducing the structural complexity of the scanning cabin. Furthermore, one or more functional components (e.g., a head fixation assembly, one or more temperature regulators, one or more anesthesia circuits, etc.) are also installed inside the cabin to ensure the fixation and temperature maintenance of the animal to be scanned within the scanning cabin, keeping the animal to be scanned in an anesthetized state with stable physiological characteristics. The method for identifying the scanning cabin provided in the embodiments of the present disclosure determines a specification parameter of the scanning cabin based on obtained coding information and preset coding information, without the need for complex sensor equipment (e.g., complex visual systems) and algorithms (e.g., complex image processing algorithms). This solves the technical problems of high identification costs and low identification efficiency of scanning cabins and improves the accuracy of scanning cabin identification. The imaging system provided in the embodiments of the present disclosure, by adopting the scanning cabin provided herein and/or applying the method for identifying the scanning cabin provided herein, reduces system complexity, improves efficiency in replacing scanning cabins based on animals to be scanned before scanning, facilitates operations of experimenters, and enhances the smoothness of the entire process of animal imaging.

Detailed descriptions of the scanning cabin, the method for identifying the scanning cabin, and the imaging system provided in the embodiments of the present disclosure will be provided below in conjunction with the accompanying drawings.

FIG. 1 is a schematic diagram of an application scenario of an imaging system according to some embodiments of the present disclosure.

As shown in FIG. 1, an imaging system 100 may be used for imaging a live animal. In some embodiments, the imaging system 100 may be applied to qualitative and quantitative research on biological processes at cellular and molecular levels in the live animal. Furthermore, imaging of the live animal through the imaging system 100 may be applied to cancer and anti-cancer drug research, immunology and stem cell research, apoptosis, pathological mechanisms, virus research, an interaction between gene expression and a protein, transgenic animal model construction, drug efficacy evaluation, drug screening and pre-clinical trial, drug formulation and dosage management, oncology application, bio-photonics detection, food supervision, environmental monitoring, or the like. As shown in FIG. 1, the imaging system 100 may include an imaging device 110, a network 120, one or more terminals 130, a processing device 140, and a storage device 150.

The imaging device 110 may be configured to scan and image a scanning object 116 to obtain relevant image(s) of the scanning object 116 for experimental analysis or diagnostic treatment. In some embodiments, the scanning object 116 may be any type of live animal, such as mice, a rabbit, a dog, a cat, etc.

As shown in FIG. 1, the imaging device 110 includes a scanning cabin 111, a scanning bed 112, a scanning cabin support arm 113, a cabin cover 114, and a scanning device 115. The scanning object 116 may be placed inside the scanning cabin 111, and the cabin cover 114 may be arranged outside the scanning cabin 111 to isolate the scanning cabin 111 from the outside environment. Further description of the imaging device 110 may be found elsewhere in the present disclosure (e.g., in FIGS. 8-12 and the related descriptions thereof), and thus will not be repeated here.

In some embodiments, data communication may be established between the scanning cabin 111 and the scanning cabin support arm 113 to facilitate the obtaining of a specification parameter of the scanning cabin 111. Based on the specification parameter of the scanning cabin 111, a resolution threshold of the imaging system may be determined, facilitating the implementation of an active collision avoidance function of the scanning device 115. Specifically, if a numerical value of a resolution inputted at a terminal is less than the resolution threshold, an adjustment of a distance between a radiation source and a detector of the scanning device 115 may be prohibited, thus avoiding collision between the radiation source and the detector of the scanning device 115 with the scanning cabin 111. In some embodiments, the scanning cabin 111 may include a connector socket, and the scanning cabin support arm 113 may have a connector plug compatible with the connector socket. When the scanning cabin 111 is connected to the scanning cabin support arm 113, the connector socket in the scanning cabin 111 connects with the connector plug on the scanning cabin support arm 113, generating coding information for the scanning cabin 111 after the connection is made. Furthermore, the imaging system 100 may include a controller (not shown in FIG. 1), which may determine the specification parameter of the scanning cabin 111 based on the coding information and preset coding information to identify the scanning cabin 111. In some embodiments, the controller may determine the resolution threshold of the imaging system 100 based on the specification parameter of the scanning cabin 111 to facilitate the implementation of the active collision avoidance function of the scanning device 115. Further description of the controller may be found elsewhere in the present disclosure (e.g., in FIG. 3 and its related descriptions), and thus will not be repeated here.

The scanning cabin 111 may move into the scanning device 115 under the drive of a feed mechanism. The scanning device 115 may be configured to scan the scanning object 116 inside the scanning cabin 111 to obtain imaging data. By way of example, the scanning device 115 may scan the scanning object 116 inside the scanning cabin 111, and the imaging system 100 may obtain the imaging data based on a scanning result of the scanning device 115. Specifically, the scanning device 115 scans the scanning object 116 inside the scanning cabin 111 to obtain the scanning data and transmits the scanning data to a computing device in the imaging system 100. The computing device processes and fuses the scanning data to generate final imaging data of the scanning object 116. In some embodiments, the final imaging data of the scanning object may include an image in DICOM format, Analyze format, NIfTI format, JPG format, PNG format, JPEG format, etc.

In some embodiments, the scanning device 115 may include at least one of a computed tomography (CT) device, a magnetic resonance (MR) device, a positron emission tomography (PET) device, or a single photon emission computed tomography (SPECT) device, or a combination thereof. By way of example, the scanning device 115 may be one or more of the CT device, the MR device, the PET device, the SPECT device, to obtain a CT image, an MR image, a PET image, a SPECT image, or a multimodal fused image of the scanning object 116 (e.g., a fused image of the CT image, the MR image, the PET image, the SPECT image, etc.). A CT device refers to a computed tomography device that obtains scanning data based on different absorption and transmission rates of X-rays by different tissues of the animal, and generates a cross-sectional or volumetric image of a scanned region using an electronic computer device. An MR device refers to a magnetic resonance imaging device that obtains image data by examining nuclei such as hydrogen (1H), carbon (13C), nitrogen (15N), fluorine (19F), sodium (23Na), phosphorus (31P), xenon (129Xe), etc., within the animal body. A PET device refers to a positron emission tomography device that obtains image data of the scanning object 116 using a radioactive tracer. A SPECT device refers to a single-photon emission computed tomography device that converts a photon into an electrical signal through a radioactive tracer to obtain image data. In some embodiments, the scanning device 115 may be a combination device such as a PET-CT device, a SPECT-CT device, a PET-MR device, a PET-SPECT-CT device, etc. It is understood that the scanning device 115 may also include other types of devices (e.g., a visible light imaging device, an ultrasound imaging device, etc.), which are not limited in embodiments of the present disclosure.

The network 120 may include a network that facilitates information exchange and/or data exchange within the imaging system 100. In some embodiments, at least one component or module (e.g., the imaging device 110, the one or more terminals 130, the processing device 140, the storage device 150, etc.) within the imaging system 100 may communicate information and/or data with at least one other component within the imaging system 100 through the network 120. For example, the processing device 140 may obtain the coding information of the scanning cabin 111 from the scanning cabin support arm 113 of the imaging device 110 via the network 120, and retrieve the preset coding information from the storage device 150 via the network 120. Then, based on the coding information and the preset coding information, the processing device 140 determines the specification parameter of the scanning cabin 111 to complete the identification of the scanning cabin 111. As another example, the processing device 140 may obtain the scanning data of the scanning object 116 from the scanning device 115 within the imaging device 110 via the network 120, and generate the imaging data of the scanning object 116 based on the scanning data. As yet another example, the processing device 140 may receive a user instruction from the one or more terminals 130 via the network 120 to execute a corresponding operation (e.g., replacing the scanning cabin 111), or send a prompt message to the one or more terminals via the network to provide a corresponding prompt to a user (e.g., prompting the user to re-enter the resolution). The network 120 may be or include a combination of a public network (e.g., the Internet), a private network (e.g., a local area network (LAN), a wide area network (WAN), etc.), a wired network (e.g., Ethernet), a wireless network (e.g., an 802.11 network, a Wi-Fi network), a cellular network (e.g., a Long-Term Evolution (LTE) network), a frame relay network, a virtual private network (VPN), a satellite network, a telephone network, a router, a hub, a switch, a server computer, etc. For example, the network 120 may include a combination of a cable network, a wired network, a fiber optic network, a telecommunications network, an intranet, a wireless LAN, a metropolitan area network (MAN), a public switched telephone network (PSTN), Bluetooth, a Zigbee network, a near field communication (NFC) network, etc. In some embodiments, the network 120 may include at least one network access point. For example, the network 120 may include a wired and/or wireless network access point such as a base station and/or an internet exchange point. At least one component of the imaging system 100 may exchange data and/or information with the network 120 via the base station and/or the internet exchange point, facilitating data and/or information exchange. In some embodiments, the data and/or information exchange between the imaging device 110, the processing device 140, and/or the storage device 150 may also be achieved through direct connections without involving the network 120.

The one or more terminals 130 may include a combination of a mobile device 130-1, a tablet 130-2, a laptop 130-3, etc. In some embodiments, the mobile device 130-1 may include a combination of a smart home device, a wearable device, a mobile device, a virtual reality device, an augmented reality device, etc. For example, the smart home device may include a smart lighting device, a control device for a smart electronic device, a smart monitoring device, a smart TV, a smart camera, an intercom, etc. The wearable device may include a wristband, a footwear, a pair of glasses, a helmet, a watch, a clothing, a backpack, a smart accessory, etc. The mobile device may include a mobile phone, a personal digital assistant (PDA), a gaming device, a navigation device, a point of sale (POS) device, a laptop, a tablet, a desktop computer, etc. The virtual reality device and/or the augmented reality device may include a virtual reality headset, a pair of virtual reality glasses, a virtual reality goggle, an augmented reality headset, a pair of augmented reality glass, an augmented reality goggle, etc. For example, the virtual reality device and/or the augmented reality device may include Google Glass, Oculus Rift, Hololens, Gear VR, etc. In some embodiments, the one or more terminals 130 may be part of the processing device 140.

The processing device 140 may control the imaging device 110 to scan the scanning object 116. For example, the processing device 140 may control the feed mechanism on the scanning bed 112 to move the scanning cabin 111. As another example, the processing device 140 may control the scanning device 115 to scan the scanning object. As yet another example, the processing device 140 may control at least one functional component in the scanning cabin 111 to perform corresponding function(s). The processing device 140 may process data and information obtained from the imaging device 110, the one or more terminals 130, and/or the storage device 150. For example, the processing device 140 may process the scanning data obtained from the scanning device 115 to generate imaging data of the scanning object 116. As another example, the processing device 140 may determine the specification parameter of the scanning cabin 111 based on real-time coding information obtained and the preset coding information to identify the scanning cabin 111. In some embodiments, the processing device 140 may be a standalone server or a server cluster, which may be centralized or distributed. In some embodiments, the processing device 140 may be local or remote. For example, the processing device 140 may obtain information and/or data from the imaging device 110 (e.g., the scanning device 115), the one or more terminals 130, and/or the storage device 150 via the network 120. As another example, the processing device 140 may directly connect to the imaging device 110 (e.g., the scanning device 115), the one or more terminals 130, and/or the storage device 150 to access the information and/or data stored therein. In some embodiments, function(s) of the processing device 140 may be implemented on a cloud platform, which may include a private cloud, a public cloud, a hybrid cloud, a community cloud, a distributed cloud, an interconnected cloud, a multi-cloud, or any combination thereof. In some embodiments, the processing device 140 may also serve as one of the one or more terminals 130 simultaneously.

In some embodiments, the processing device 140 may include one or more sub-processing devices (e.g., a single-core processor or a multi-core processor). For example, the processing device 140 may include a central processing unit (CPU), an application-specific integrated circuit (ASIC), an application-specific instruction processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction set computer (RISC), a microprocessor, or any combination thereof.

The storage device 150 may store data, instructions, and/or other information. In some embodiments, the storage device 150 may store data obtained from the one or more terminals 130 and/or the processing device 140. In some embodiments, the storage device 150 may store data and/or instructions that may be used or executed by the processing device 140 to implement exemplary methods described in the present disclosure. The storage device 150 may include high-capacity storage, removable storage, volatile read-write memory, read-only memory (ROM), or any combination thereof. In some embodiments, the high-capacity storage may include a disk, an optical disk, a solid-state drive, etc. The removable storage may include a flash drive, a floppy disk, an optical disk, a memory card, a zip disk, a tape, etc. The volatile read-write memory may include random-access memory (RAM), which includes dynamic RAM (DRAM), double data rate synchronous DRAM (DDR SDRAM), static RAM (SRAM), thyristor RAM (T-RAM), zero-capacitor RAM (Z-RAM), etc. The ROM may include mask ROM (MROM), programmable ROM (PROM), erasable programmable ROM (EPROM), electrically erasable programmable ROM (EEPROM), compact disk read-only memory (CD-ROM), digital versatile disk read-only memory, etc. The functionality of the storage device 150 may be implemented on a cloud platform. For example, the cloud platform may include a private cloud, a public cloud, a hybrid cloud, a community cloud, a distributed cloud, an interconnected cloud, a multi-cloud, or any combination thereof.

In some embodiments, the storage device 150 may be connected to the network 120, thereby communicating with at least one component (e.g., the processing device 140, the one or more terminals 130, the imaging device 110, etc.) of the imaging system 100. At least one component of the imaging system 100 may obtain data or instructions stored in the storage device 150 via the network 120. In some embodiments, the storage device 150 may directly connect or communicate with at least one component (e.g., the processing device 140, the one or more terminals 130, the imaging device 110, etc.) of the imaging system 100. In some embodiments, the storage device 150 may be part of the processing device 140.

The imaging system 100 provided in the embodiments of the present disclosure may be used to implement a method for identifying a scanning cabin provided in the embodiments of the present disclosure. Specifically, the method for identifying the scanning cabin in the embodiments of the present disclosure may be executed on the one or more terminals, the computing device, the processing device, or similar computing devices included in the imaging system 100. For example, the method for identifying the scanning cabin provided in the embodiments of the present disclosure may be executed on a terminal. Below is an illustrative description of an operation of the method for identifying the scanning cabin on a terminal.

Figure 2:
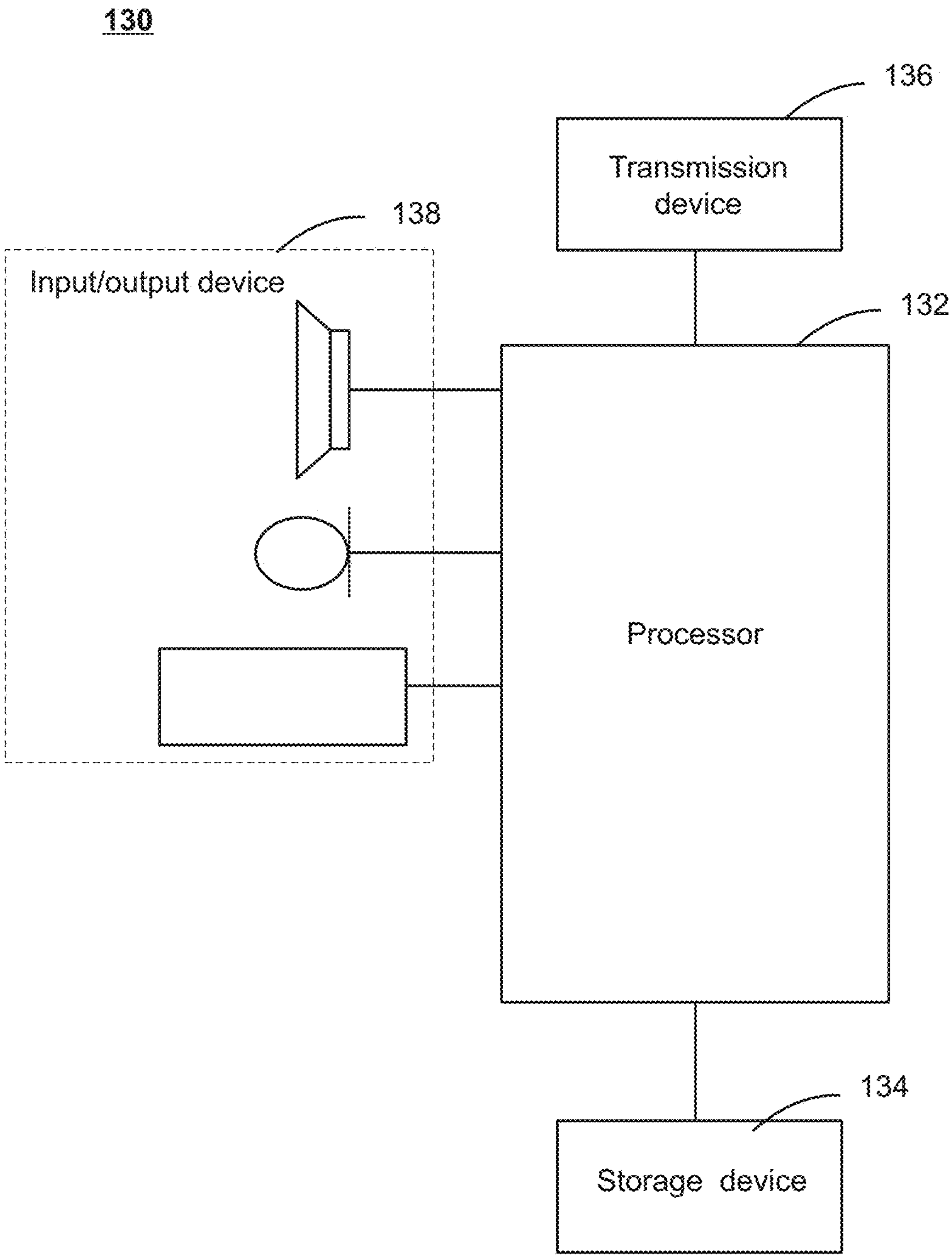
FIG. 2 is a schematic diagram illustrating an exemplary hardware structure of a terminal used for implementing a method for identifying a scanning cabin according to some embodiments of the present disclosure.

FIG. 2 is a schematic diagram illustrating an exemplary hardware structure of a terminal used for implementing a method for identifying a scanning cabin according to some embodiments of the present disclosure.

Figure 3:
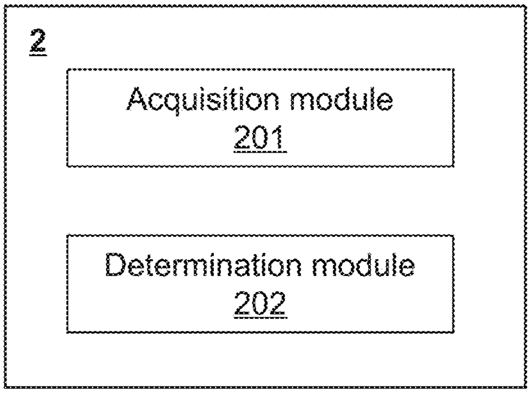
FIG. 3 is a block diagram of a controller according to some embodiments of the present disclosure.

As shown in FIG. 2, the terminal 130 may include one or more processors 132 (only one is shown in FIG. 3) and a storage device 134 for storing data (e.g., preset coding information, a plurality of specification parameters of the scanning cabin, or a correspondence between a plurality of pieces of preset coding information and the plurality of specification parameters of the scanning cabin).

In some embodiments, the one or more processors 132 may include, but are not limited to, a processing device such as a microprocessor (e.g., a microcontroller unit (MCU)) or a programmable logic device (e.g., a field-programmable gate array (FPGA)). In some embodiments, the one or more processors 132 may be the processing device 140 or a part thereof as shown in FIG. 1. In some embodiments, the terminal 130 may also include a transmission device 136 and an input/output device 138 for communication functions. It is to be understood that the structure of the terminal 130 shown in FIG. 2 is illustrative only and is not intended to limit the structure of the one or more terminals 130 for executing the method for identifying the scanning cabin provided in the embodiments of the present disclosure. For example, the one or more terminals for executing the method for identifying the scanning cabin provided in the embodiments of the present disclosure may include more or fewer components than that shown in FIG. 2, or may have a different configuration from that shown in FIG. 2.

In some embodiments, the storage device 134 may be configured to store one or more computer programs, such as one or more application software programs and modules and one or more computer programs corresponding to the method for identifying the scanning cabin provided in the embodiments of the present disclosure. By running the one or more computer programs stored in the storage device 134, the one or more processors 132 may execute various functional applications and data processing, thereby implementing the method for identifying the scanning cabin provided in the embodiments of the present disclosure. In some embodiments, the storage device 134 may include high-speed random-access memory. In some embodiments, the storage device 134 may further include non-volatile memory, such as one or more magnetic storage devices, flash memory, or other non-volatile solid-state storage devices. In some embodiments, the storage device 134 may also include storage set remotely from the one or more processors 132, which may be connected to the terminal 130 via a network (e.g., the network 120 shown in FIG. 1). In some embodiments, the network connecting the remote storage and the terminal 130 may include, but is not limited to, the Internet, an enterprise intranet, a local area network (LAN), a mobile communication network, or a combination thereof. In some embodiments, the storage device 134 may be the storage device 150 or a part thereof as shown in FIG. 1.

In some embodiments, the transmission device 136 is configured to receive or send data via a network. In some embodiments, the network may include a wireless network provided by a communication provider of the terminal 130. In some embodiments, the transmission device 136 may include a network interface controller (NIC), which may communicate with the Internet through a base station and other network devices. In some embodiments, the transmission device 136 may be a radio frequency (RF) module used for wireless communication with the Internet.

FIG. 3 is a block diagram of a controller according to some embodiments of the present disclosure. As shown in FIG. 3, a controller 2 may include an acquisition module 201 and a determination module 202.

In some embodiments, the acquisition module 201 may be configured to obtain coding information of a scanning cabin (e.g., the scanning cabin 111 shown in FIG. 1). In some embodiments, the coding information of the scanning cabin may be preset identification information used to identify a category of the scanning cabin. For example, the coding information may be used to identify a type, a size, an applicable scanning object, a scanning parameter (e.g., a maximum resolution), etc., of the scanning cabin, or a combination thereof. In some embodiments, the coding information of the scanning cabin may include one or more elements such as a text, a symbol, a letter, a number, etc. In some embodiments, the coding information of the scanning cabin may be represented in ASCII encoding, Unicode, UTF-8, UTF-16, etc.

In some embodiments, the scanning cabin may include an I/O module which includes a plurality of I/O interfaces, and the coding information of the scanning cabin may include status values of the plurality of I/O interfaces of the I/O module. In some embodiments, the status values of the plurality of I/O interfaces may include a status value of each of the plurality of I/O interfaces and a positional sequence of the plurality of I/O interfaces. Furthermore, the acquisition module 201 may obtain the status values of the plurality of I/O interfaces based on a wiring manner of the plurality of I/O interfaces.

In some embodiments, the determination module 202 may determine a specification parameter of the scanning cabin based on the coding information and preset coding information. The preset coding information may include a plurality of pieces of coding information corresponding to a certain category of scanning cabins pre-stored in a database. Specifically, each piece of the plurality of preset coding information may correspond to the specification parameter of a single scanning cabin. In some embodiments, the determination module 202 may directly determine the specification parameter of the scanning cabin based on the coding information obtained from the scanning cabin. In some embodiments, the determination module 202 may determine, from a plurality of pieces of the preset coding information, whether a piece of preset coding information corresponding to the coding information exists in the database. In response to a determination that the piece of preset coding information corresponding to the coding information exists in the database, the determination module 202 may obtain the specification parameter of the scanning cabin corresponding to the piece of preset coding information from the database.

In some embodiments, the determination module 202 may establish a correspondence between a plurality of pieces of preset coding information and a plurality of specification parameters of a plurality of scanning cabins, and store the correspondence between the plurality of pieces of preset coding information and the plurality of specification parameters of the plurality of scanning cabins in the database.

In some embodiments, the determination module 202 may determine one or more scanning parameters corresponding to the scanning cabin based on the specification parameter of the scanning cabin. In some embodiments, the determination module 202 may determine the one or more scanning parameters corresponding to the scanning cabin based on the coding information of the scanning cabin. In some embodiments, the one or more scanning parameters may include a resolution threshold corresponding to the scanning cabin, wherein the resolution threshold corresponding to the scanning cabin refers to a numerical value of a maximum resolution supported by an imaging system provided with the scanning cabin.

In some embodiments, the determination module 202 may include a resolution acquisition submodule, a determination submodule, and an output submodule. The resolution acquisition submodule may be configured to obtain a resolution inputted through a terminal (e.g., the one or more terminals 130). The determination submodule may be configured to determine whether the numerical value of the obtained resolution is less than the resolution threshold. In response to a determination that the resolution is less than the resolution threshold, the output submodule may output a prompt message to suggest re-entering the resolution or replacing the scanning cabin, or set a value range of the resolution inputted through the terminal device based on the resolution threshold. In some embodiments, the resolution obtained by the resolution acquisition submodule may be the real-time resolution inputted by a user through the terminal. In some embodiments, the imaging system may scan and image a scanning object in the scanning cabin based on the resolution obtained by the resolution acquisition submodule. In some embodiments, the resolution threshold refers to the numerical value of the maximum resolution supported by the imaging system. In some embodiments, the resolution threshold is at least related to the scanning cabin. Furthermore, if the determination submodule determines that the numerical value of the resolution inputted through the terminal is less than the resolution threshold, the imaging system may prohibit an adjustment of a distance between a radiation source (e.g., a tube) and a detector of a scanning device (e.g., a CT device) to prevent collision between the radiation source or the detector of the scanning device with the scanning cabin, thereby implementing an active collision avoidance function of the imaging system. At the same time, the output submodule may output the prompt message to suggest re-entering a resolution value less than the resolution threshold or replacing the scanning cabin to reduce the resolution threshold of the scanning cabin to a value lower than the resolution inputted through the terminal.

It should be noted that the description of the imaging system and its modules above is for descriptive convenience and does not limit the scope of the present disclosure to the embodiments described. It may be understood that for those skilled in the art, after understanding the principle of the system, various modules may be arbitrarily combined or constitute subsystems connected to other modules without departing from this principle. In some embodiments, the acquisition module 201 and the determination module 202 disclosed in FIG. 3 or each submodule of the determination module 202 may be different modules in a system, or one module may implement the functions of two or more of the above modules. For example, the modules may share a storage module, and each module may also have its own storage module. Such variations are within the scope of protection of the present disclosure.

The imaging system provided in the embodiments of the present disclosure achieves better scalability and compatibility by setting the scanning cabin as replaceable, enabling the replacement of the scanning cabin corresponding to different scanning objects. Furthermore, by identifying the scanning cabin (e.g., determining the specification parameter of the scanning cabin), the active collision avoidance function of the imaging system can be implemented. In some embodiments, the imaging system may obtain relevant feature information of the scanning cabin by collecting visual information, further identifying the scanning cabin based on the relevant feature information to determine the scanning cabin corresponding to the relevant feature information. For example, the imaging system may capture image(s) of the scanning cabin using a corresponding imaging device (e.g., a camera), then use image processing algorithm(s) to recognize feature(s) in the obtained image(s) to obtain image feature(s) that may characterize a category (e.g., the specification parameter) of the scanning cabin, and then determine the specification parameter of the scanning cabin based on the image feature(s) to achieve the identification of the scanning cabin. In some embodiments, the imaging system may directly obtain information related to the category (e.g., the specification parameter) of the scanning cabin by scanning the QR code or barcode on the scanning cabin using a barcode scanner, or by using radio frequency signal(s) to communicate with a card reader, scanning an electronic tag on the scanning cabin, and directly obtaining information related to the category (e.g., the specification parameter) of the scanning cabin included in the electronic tag, to determine the category of the scanning cabin, thereby achieving the identification of the scanning cabin. Of course, whether through the collection of visual information of the scanning cabin or the scanning of QR codes or barcodes or electronic tags, it is necessary to rely on a complex sensor device (e.g., a camera, a card reader, etc.), a computing device, and an algorithms (e.g., an image processing algorithm, a decoding algorithm, etc.) to complete, which results in higher identification costs, lower identification efficiency, and a risk of misjudgment. Some embodiments of the present disclosure provide a method for identifying a scanning cabin that accurately identifies the scanning cabin by obtaining the coding information of the scanning cabin, and then determining the specification parameter of the scanning cabin based on the coding information of the scanning cabin and preset coding information, eliminating the need for complex devices. The method is simple, has a relatively high identification efficiency, and a relatively low identification cost.

The method for identifying the scanning cabin provided in some embodiments of the present disclosure will be described in detail below.

Figure 4:
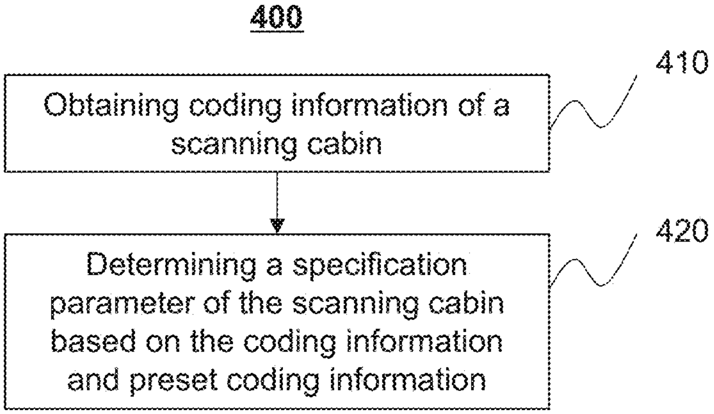
FIG. 4 is a flowchart of an exemplary process for identifying a scanning cabin according to some embodiments of the present disclosure.

FIG. 4 is a flowchart of an exemplary process for identifying a scanning cabin according to some embodiments of the present disclosure. As shown in FIG. 4, process 400 may include one or more of the following operations.

In 410, coding information of the scanning cabin may be obtained. Operation 410 may be performed by the acquisition module 201.

In some embodiments, different scanning cabins may correspond to different pieces of coding information, therefore, by obtaining a piece of coding information of a scanning cabin, a category of the scanning cabin corresponding to the piece of coding information may be determined. The scanning cabin is used to place a scanning object. Due to the difference in types, sizes, postures, etc., of scanning objects, specification parameters of the corresponding scanning cabins also vary. It is necessary to select an appropriate scanning cabin based on the type, the size, the posture, etc., of the scanning object. In some embodiments, the coding information may be identification information used to identify the category of the scanning cabin. In some embodiments, the coding information may be pre-set based on the category of the scanning cabin, that is, different categories of scanning cabins may have different pieces of coding information. In some embodiments, the coding information may include one of a text, a symbol, a letter, or a number, or a combination thereof.

In some embodiments, the acquisition module 201 may obtain the coding information of the scanning cabin by connecting a connector plug on the scanning cabin and a connector socket on other components (e.g., a scanning cabin support arm) of an imaging system. Specifically, the connector plug may be provided on the scanning cabin, and the corresponding connector socket may be provided on the scanning cabin support arm. The connection between the connector plug and the connector socket may generate the coding information of the scanning cabin to be obtained by the acquisition module 201. The connection manner between the connector plug and the connector socket corresponds to the coding information of the scanning cabin, that is, when different categories of scanning cabins are connected to the scanning cabin support arm, the connection manners between the connector plug and the connector socket are different. The acquisition module 201 may determine the coding information corresponding to the scanning cabin based on the connection manner between the connector plug and the connector socket. In some embodiments, the connector plug may include a plurality of I/O interfaces, and the connector socket may include a plurality of pins used to read status values (e.g., voltage levels) of the plurality of I/O interfaces, wherein the status values of the plurality of I/O interfaces may serve as the coding information of the scanning cabin. In some embodiments, the connection manner between the connector plug and the connector socket may include a count and/or a sequence of connections between the plurality of I/O interfaces in the connector plug and the plurality of pins in the connector socket (referred to as a wiring manner of the plurality of I/O interfaces). More descriptions on obtaining the coding information when the coding information includes the status values of the plurality of I/O interfaces will be provided below.

In some embodiments, the scanning cabin may include an I/O module, which may include the plurality of I/O interfaces. The coding information of the scanning cabin may include the status values of the plurality of I/O interfaces of the I/O module. In some embodiments, the I/O module may serve as an input/output module of the scanning cabin, and may be installed in a cabin of the scanning cabin, and connected to and communicate with other components (e.g., the scanning cabin support arm) of the imaging system in a contact or non-contact manner. In some embodiments, the I/O module has a plug-and-play structure, allowing for quick insertion and removal operations of the I/O module in the imaging system through the installation and removal of the scanning cabin. As an illustrative example, the connector plug on the scanning cabin may include the I/O module, and through the insertion and removal operations of the connector plug and the connector socket on the scanning cabin support arm, the installation and removal of the scanning cabin and the scanning cabin support arm may be achieved. When the connector socket and the connector plug are connected, the acquisition module 201 may obtain the status values of the plurality of I/O interfaces of the I/O module based on the connection manner between the connector socket and the connector plug (e.g., the wiring manner of the plurality of I/O interfaces). In some embodiments, the I/O module may be a wireless communication module, which may perform data transmission based on a wireless transmission channel without requiring a contact-based connection with other components of the imaging system.

In some embodiments, the status values of the plurality of I/O interfaces of the I/O module may serve as the coding information of the scanning cabin. In some embodiments, the status values of the plurality of I/O interfaces may include a status value of each I/O interface in the plurality of I/O interfaces and a positional sequence of the plurality of I/O interfaces. In some embodiments, the status value of each I/O interface in the plurality of I/O interfaces may be arranged and combined according to the positional sequence of the plurality of I/O interfaces to form the status values of the plurality of I/O interfaces. In some embodiments, different status values may be determined based on different I/O interfaces of the I/O module, that is, the status value of each I/O interface in the plurality of I/O interfaces may be different. In some embodiments, different I/O interfaces may output different numerical values as their status values. In some embodiments, the status values of the plurality of I/O interfaces may be represented by voltage levels of the I/O interfaces, in which the voltage levels may include high and low voltage levels. In some embodiments, the voltage levels of the I/O interfaces may be represented by Boolean quantities (i.e., binary codes), in which the high voltage level may be represented by "1" and the low voltage level may be represented by "0". In some embodiments, the positional sequence of the plurality of I/O interfaces may be fixed or default. In some embodiments, the positional sequence of the plurality of I/O interfaces may be predetermined based on positions of the plurality of pins used to read the status values of the plurality of I/O interfaces. As an illustrative example, the connector plug on the scanning cabin may be provided with the plurality of I/O interfaces, and the corresponding connector socket on the scanning cabin support arm may be provided with the plurality of pins used to read the status values of the plurality of I/O interfaces, where the positional sequence of the plurality of I/O interfaces may be predetermined based on the setting of the positions of the corresponding pins on the connector socket. In some embodiments, when the imaging system replaces the scanning cabin, it may be necessary to re-obtain the positional sequence of the plurality of I/O interfaces in the I/O module of the scanning cabin.

In some embodiments, after a computer system reads the status values of the plurality of I/O interfaces of the I/O module (i.e., the coding information of the scanning cabin), the obtained status values are matched with I/O encoding values (i.e., the preset coding information) recorded in the computer system to obtain the specification parameter corresponding to the scanning cabin.

The scanning cabin in the embodiments of the present disclosure includes the I/O module, and the coding information of the scanning cabin includes the status values of the plurality of I/O interfaces of the I/O module. By obtaining the status values of the plurality of I/O interfaces of the I/O module to acquire the coding information of the scanning cabin, the system has a simple structure, low computational cost, and easy implementation of digital encoding, thereby improving the efficiency of scanning cabin identification.

In some embodiments, the I/O module includes the plurality of I/O interfaces, and obtaining the coding information of the scanning cabin may include the following operation(s).

The status values of the plurality of I/O interfaces corresponding to the wiring manner may be obtained, based on the wiring manner of the plurality of I/O interfaces.

In some embodiments, the acquisition module 201 may determine the status values of the plurality of I/O interfaces based on the wiring manner of the plurality of I/O interfaces. Different wiring manners correspond to different status values of the plurality of I/O interfaces. In some embodiments, the wiring manner of the plurality of I/O interfaces refers to a count and a sequence of I/O interfaces participating in the wiring.

Figure 5:
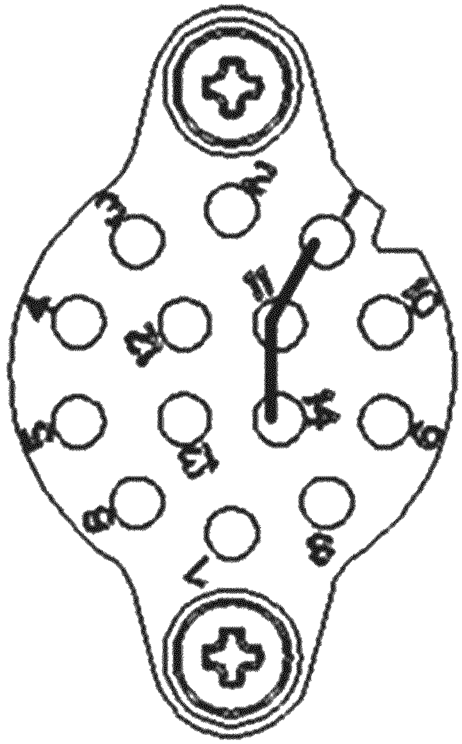
FIG. 5 is a schematic diagram of a wiring manner of an I/O module according to some embodiments of the present disclosure.

FIG. 5 is a schematic diagram of a wiring manner of an I/O module according to some embodiments of the present disclosure.

As an illustrative example, as shown in FIG. 5, the I/O module may include fourteen I/O interfaces numbered 1-14 respectively, wherein the numbering of the fourteen I/O interfaces represents a positional sequence of the fourteen I/O interfaces. Status values corresponding to the fourteen I/O interfaces under different wiring manners are also different. For example, when interfaces numbered 1, 11, and 14 are connected, "01 11 14" or the corresponding binary number "0001 1011 1101" may be designated as the status value corresponding to this wiring manner. As another example, when interfaces numbered 1, 2, 10, and 14 are connected, "01 02 10 14" or the corresponding binary number "0001 0010 1010 1100" may be designated as the status value corresponding to this wiring manner.

In some embodiments, when a plurality of I/O interfaces adopt a certain wiring manner, a combination of voltage levels of the plurality of interfaces may be designated as the status value of the plurality of interfaces corresponding to that wiring manner. The voltage levels of interfaces participating in the wiring manner may be relatively high (represented as "1"), while the voltage levels of interfaces not participating in the wiring manner may be relatively low (represented as "0"). For example, when interfaces numbered 1, 11, and 14 are connected, the combination of the voltage levels of the interfaces 1-14 may be "10000000001001", which may be used to represent the status value corresponding to this wiring manner. As another example, when interfaces numbered 1, 2, 10, and 14 are connected, "11000000010001" may be designated as the status value corresponding to this wiring manner.

In some embodiments, a count of wiring manners for the plurality of I/O interfaces may be related to a total count of the plurality of I/O interfaces and a count of I/O interfaces participating in the wiring (or a count of pins used to read the status values of the I/O interfaces). It may be understood that by modifying the wiring manner of the plurality of I/O interfaces, such as adjusting the total count of the plurality of I/O interfaces and/or the count of pins used to read the status values of the I/O interfaces, different status values may be set for the plurality of I/O interfaces. For example, as shown in FIG. 5, if the count of pins used to read the status values of the I/O interfaces is 3, the fourteen I/O interfaces may have 14×13×12 wiring manners. As another example, if the count of pins is 4, the fourteen I/O interfaces may have 14×13×12×11 wiring manners. It should be noted that the total count of the plurality of I/O interfaces and the count of I/O interfaces participating in the wiring shown in FIG. 5 are only examples and are not intended to be limiting. In some embodiments, the total count of I/O interfaces and the count of I/O interfaces participating in the wiring in the I/O module may be set according to actual needs (i.e., depending on a count of different categories or specification parameters of scanning cabins).

In practical application scenarios, a preset count of wiring manners may be selected, and the corresponding status values may be further set. Then, the status values may be designated as the preset coding information associated with a corresponding scanning cabin. Subsequently, based on the coding information of the scanning cabin and the preset coding information, a specification parameter of the scanning cabin can be determined.

In the embodiments of the present disclosure, the status values of the plurality of I/O interfaces corresponding to the wiring manners of the plurality of I/O interfaces are obtain. By determining the status values of the plurality of I/O interfaces based on the wiring manners of the plurality of I/O interfaces as the coding information of the scanning cabin, without adding additional status value acquisition modules, multiple wiring manners can be selected based on actual needs, and the wiring manners are easy to distinguish and identify, reducing the cost of scanning cabin identification.

In 420, the specification parameter of the scanning cabin may be determined based on the coding information and the preset coding information. Operation 420 may be executed by the determination module 202.

In some embodiments, the specification parameter of the scanning cabin may correspond to a piece of the coding information and/or a piece of the preset coding information. In some embodiments, the specification parameter of the scanning cabin may include a shape, a size, a scanning intensity, and a load-bearing capacity (i.e., a weight of the scanning object that the scanning cabin can bear) of the scanning cabin, and a maximum resolution supported by the imaging system that includes the scanning cabin, or a combination thereof.

In some embodiments, after the acquisition module 201 obtains the coding information of the scanning cabin, the determination module 202 may directly determine the specification parameter of the scanning cabin based on the coding information of the scanning cabin. In some embodiments, the coding information of the scanning cabin may be a code (e.g., ASCII code, Unicode, UTF-8, UTF-16, etc.) including information relevant to the specification parameter of the scanning cabin, and the determination module 202 may use a corresponding decoding algorithm to decode the coding information of the scanning cabin to obtain the specification parameter of the scanning cabin.

In some embodiments, the determination module 202 may determine the specification parameter of the scanning cabin based on the coding information and the preset coding information. Furthermore, the determination module 202 may determine, from a plurality of pieces of the preset coding information, whether a piece of preset coding information corresponding to the coding information exists in a database, wherein each piece of the plurality of pieces of preset coding information corresponds to a specification parameter of a single scanning cabin. In response to a determination that the piece of preset coding information corresponding to the coding information exists in the database, the determination module 202 may obtain the specification parameter of the scanning cabin corresponding to the piece of preset coding information from the database. More descriptions regarding how the determination module 202 determines the specification parameter of the scanning cabin based on the coding information and preset coding information may be found in the description of process 600.

In some embodiments, the determination module 202 may directly determine the specification parameter of the scanning cabin based on an image of the scanning cabin. As an illustrative example, the determination module 202 may use an image processing algorithm to recognize feature(s) of the image of the scanning cabin, thereby determining the specification parameter of the scanning cabin based on the image feature(s).

Figure 6:
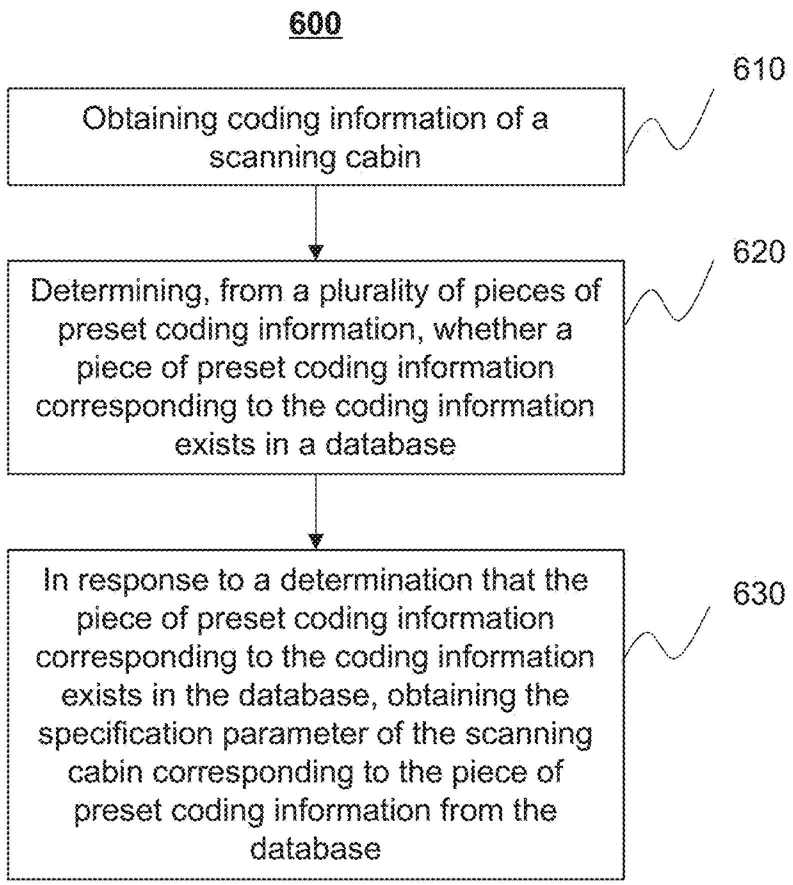
FIG. 6 is a flowchart of an exemplary process for identifying a scanning cabin according to some embodiments of the present disclosure.

FIG. 6 is a flowchart of an exemplary process for identifying a scanning cabin according to some embodiments of the present disclosure. As shown in FIG. 6, process 600 may include one or more of the following operations.

In 610, coding information of the scanning cabin may be obtained. Operation 610 may be executed by the acquisition module 201. More descriptions of the operation 610 may be found in operation 410 in process 400, which will not be repeated here.

In 620, whether a piece of preset coding information corresponding to the coding information exists in a database may be determined. Operation 620 may be executed by the determination module 202.

In some embodiments, after the acquisition module 201 obtains the coding information of the scanning cabin, the determination module 202 may search the database to determine whether the piece of preset coding information corresponding to the coding information exists in the database. The preset coding information is predefined and corresponds to a category of scanning cabins, and is used to identify the scanning cabins of the category. Furthermore, each piece of preset coding information corresponds to a specification parameter of a single scanning cabin. In some embodiments, each piece of preset coding information and the corresponding specification parameter of the scanning cabin may be pre-stored in the database for subsequent retrieval and matching of the piece of coding information of the scanning cabin against the plurality of pieces of the preset coding information in the database.

In 630, in response to a determination that the piece of preset coding information corresponding to the coding information exists in the database, the specification parameter of the scanning cabin corresponding to the piece of preset coding information may be obtained from the database. Operation 630 may be executed by the determination module 202.

In some embodiments, in response to a determination that the determination module 202 retrieves the piece of preset coding information corresponding to the coding information from the database, the specification parameter of the scanning cabin corresponding to the piece of preset coding information may be obtained from the database. It may be understood that the specification parameter of the scanning cabin corresponding to the piece of preset coding information is the specification parameter of the scanning cabin obtained from the coding information. In some embodiments, based on the specification parameter of the scanning cabin corresponding to the preset coding information, the imaging system may determine a scanning mode, scanning steps, a scanning parameter, etc., for a scanning object. In some embodiments, the scanning mode for the scanning object by an imaging system may be related to a scanning device in the imaging system. For example, if the scanning device is a CT scanner, the scanning mode for the scanning object by the imaging system may include positioning scanning, axial tomography scanning, continuous scanning, helical scanning, etc. In some embodiments, the scanning steps for the scanning object by the imaging system refers to operational procedures of the imaging system. In some embodiments, the scanning parameter for scanning by the imaging system may include a scanning intensity (e.g., a radiation dose, a tube current, etc.), a resolution, a field of view, the scanning mode, or a combination thereof. In some embodiments, the scanning mode may include CT imaging, MR imaging, PET imaging, SPECT imaging, ultrasound imaging, visible light imaging, etc.

In some embodiments, in response to a determination that the determination module 202 does not retrieve the piece of preset coding information corresponding to the coding information from the database, there are at least two possible scenarios. First, a new scanning cabin has been introduced into the imaging system, meaning that no preset coding information corresponding to the newly introduced scanning cabin is stored in the database, and the specification parameter of the scanning cabin does not exist in the database. In this case, the determination module 202 may output a prompt message, for example, outputting the prompt message to a terminal, to prompt a user to set a piece of preset coding information corresponding to the scanning cabin, and to save the piece of preset coding information and the specification parameter of the scanning cabin to the database. Second, a malfunction occurs in the imaging system, causing the acquisition module 201 to fail to accurately obtain or match the coding information of the scanning cabin. In this case, the imaging system may output a fault message to prompt the user to address the system malfunction.

The method for identifying the scanning cabin provided in the embodiments of the present disclosure determines, from a plurality of pieces of the preset coding information, whether the piece of preset coding information corresponding to the coding information exists in the database by obtaining the coding information of the scanning cabin. Each piece of the plurality of pieces of preset coding information corresponds to a specification parameter of a single scanning cabin. In response to a determination that the piece of preset coding information corresponding to the coding information exists in the database, the specification parameter of the scanning cabin corresponding to the piece of preset coding information is obtained from the database to serve as the specification parameter of the scanning cabin in the imaging system. By determining the specification parameter of the scanning cabin based on its coding information, the system can address technical issues such as a relatively high identification cost, a relatively low identification efficiency, and the risk of misjudgment in identifying scanning cabins in imaging systems. The method does not require complex devices and is simple to implement, reducing the identification costs of scanning cabins and improving the identification efficiency.

In some embodiments, before determining whether the piece of preset coding information corresponding to the coding information exists in the database, the method may further include: establishing a correspondence between the plurality of pieces of preset coding information and a plurality of specification parameters of a plurality of scanning cabins, and storing the correspondence between the plurality of pieces of preset coding information and the plurality of specification parameters of the plurality of scanning cabins in the database.

In some embodiments, the determination module 202 may establish a correspondence between the plurality of scanning cabins and the plurality of pieces of preset coding information, associate the plurality of specification parameters of the plurality of scanning cabins with the plurality of pieces of the preset coding information, establish the correspondence between the plurality of pieces of preset coding information and the plurality of specification parameters of the plurality of scanning cabins, and store the correspondence in the database. In some embodiments, the determination module 202 may assign a piece of preset coding information for each category of scanning cabin to identify that category of scanning cabin, then obtain the specification parameter of the category of scanning cabin, and establish the correspondence between the specification parameter of the category of scanning cabin and the piece of preset coding information. The preset coding information and the corresponding specification parameter of the scanning cabin may be stored in the same storage unit (e.g., the storage device 150 shown in FIG. 1 or the storage device 134 shown in FIG. 2), facilitating direct querying of the specification parameter of the corresponding scanning cabin based on the preset coding information.

In some embodiments, the method for identifying the scanning cabin provided in the present disclosure may further include determining one or more scanning parameters corresponding to the scanning cabin based on the specification parameter of the scanning cabin.

In some embodiments, after the determination module 202 obtains the specification parameter of the scanning cabin, it may further determine the one or more scanning parameters corresponding to the scanning cabin based on the specification parameter of the scanning cabin. It may be understood that due to differences in the size and posture of different scanning objects, the specification parameter of the scanning cabin for the different scanning objects may also be different. Therefore, different scanning parameters are needed for scanning objects with different scanning cabins to achieve the best scanning effect. Specifically, different scanning intensities, resolutions, scanning modes, etc., are used for scanning different objects to obtain scanning images under different modalities such as CT images, PET images, SPECT images, etc., under different scanning intensities and/or resolutions.

In some embodiments, the determination module 202 may directly determine the one or more scanning parameters corresponding to the scanning cabin based on the coding information of the scanning cabin and the preset coding information. For example, the determination module 202 may directly determine the one or more scanning parameters corresponding to the scanning cabin based on the coding information. As another example, the determination module 202 may determine, from the plurality of pieces of the preset coding information, whether the piece of preset coding information corresponding to the coding information exists in the database. In response to a determination that the piece of preset coding information corresponding to the coding information exists in the database, the determination module 202 may obtain the one or more scanning parameters corresponding to the scanning cabin from the database. In some embodiments, the determination of the specification parameter and the one or more scanning parameters of the scanning cabin may be performed sequentially. In some embodiments, the one or more scanning parameters corresponding to the scanning cabin may include a resolution threshold corresponding to the scanning cabin.

In some embodiments, the method for identifying the scanning cabin provided in the present disclosure may further include obtaining a resolution inputted through a terminal device (e.g., the one or more terminals 130), determining whether the resolution is less than the resolution threshold of the scanning cabin, and in response to a determination that the resolution is less than the resolution threshold, providing a prompt message to suggest re-entering the resolution or replacing the scanning cabin. The resolution threshold refers to a numerical value of a maximum resolution supported by an imaging device (e.g., the imaging device 110 shown in FIG. 1). In some embodiments, the resolution threshold of the imaging device may be considered as a resolution threshold of an imaging system that includes the imaging device. In some embodiments, the imaging system may set a resolution during a scanning process based on the resolution inputted through the terminal, and a resolution obtained in a scanning image is the resolution for the imaging system. The smaller a numerical value of the resolution of the scanning image, the higher the resolution of the scanning image. In other words, when the imaging system performs imaging with the resolution inputted through the terminal, the smaller the numerical value of the resolution, the higher the resolution of the obtained scanning image. Furthermore, when the imaging system obtains a scanning image with the maximum resolution at a certain resolution during scanning, the numerical value of this resolution becomes the resolution threshold of the imaging system.

In some embodiments, before scanning the scanning object, the resolution acquisition submodule of the determination module 202 may receive and obtain the resolution input through the terminal. Then, the determination submodule determines whether the numerical value of the resolution is less than the resolution threshold, that is, whether the resolution exceeds the maximum resolution supported by the imaging system. In response to a determination that the numerical value of the resolution is less than the resolution threshold, i.e., the resolution exceeds the maximum resolution, the output submodule may output the prompt message. The prompt message may be sent to the terminal and displayed on the terminal to prompt the user to re-enter the resolution or to replace the scanning cabin with a scanning cabin having a different specification parameter. In some embodiments, the imaging system may set a value range of the resolution inputted through the terminal device based on the resolution threshold. For example, the value range of the resolution inputted through the terminal may be greater than or equal to the resolution threshold, allowing the numerical value of the resolution inputted through the terminal to be greater than the resolution threshold.

In some embodiments, before obtaining the resolution inputted through the terminal, it may be necessary to determine the resolution threshold of the imaging system. Specifically, the resolution threshold of the imaging system is at least related to the scanning cabin and the scanning device included therein. By way of example, in the imaging system, the scanning device may be a CT device, which typically includes a gantry, an X-ray tube, and a detector mounted on the gantry. The X-ray tube includes an X-ray emission window and a filter. The X-ray tube emits an X-ray through the emission window, which passes through the filter to penetrate a certain thickness of a layer of a region on a scanning object before being received by the detector. Furthermore, the resolution threshold may be determined based on a first distance from the X-ray emission window of the scanning device to the detector of the scanning device, a second distance from the X-ray emission window to the filter of the scanning device, and a pixel size of the detector. The second distance from the X-ray emission window to the filter may be determined by a third distance from the X-ray emission window to a rotation center of the scanning cabin and an outer diameter of the scanning cabin. By obtaining the first distance from the X-ray emission window of the scanning device to the detector of the scanning device, the second distance from the X-ray emission window to the filter of the scanning device, the third distance from the X-ray emission window to the rotation center of the scanning cabin, and the pixel size of the detector of the scanning device, the resolution threshold of the imaging system may be determined based on the first distance, the second distance, the third distance, and the pixel size of the detector. In some embodiments, the determination module 202 may be configured to determine the specification parameter of the scanning cabin, thereby determining the outer diameter of the scanning cabin.

Figure 7:
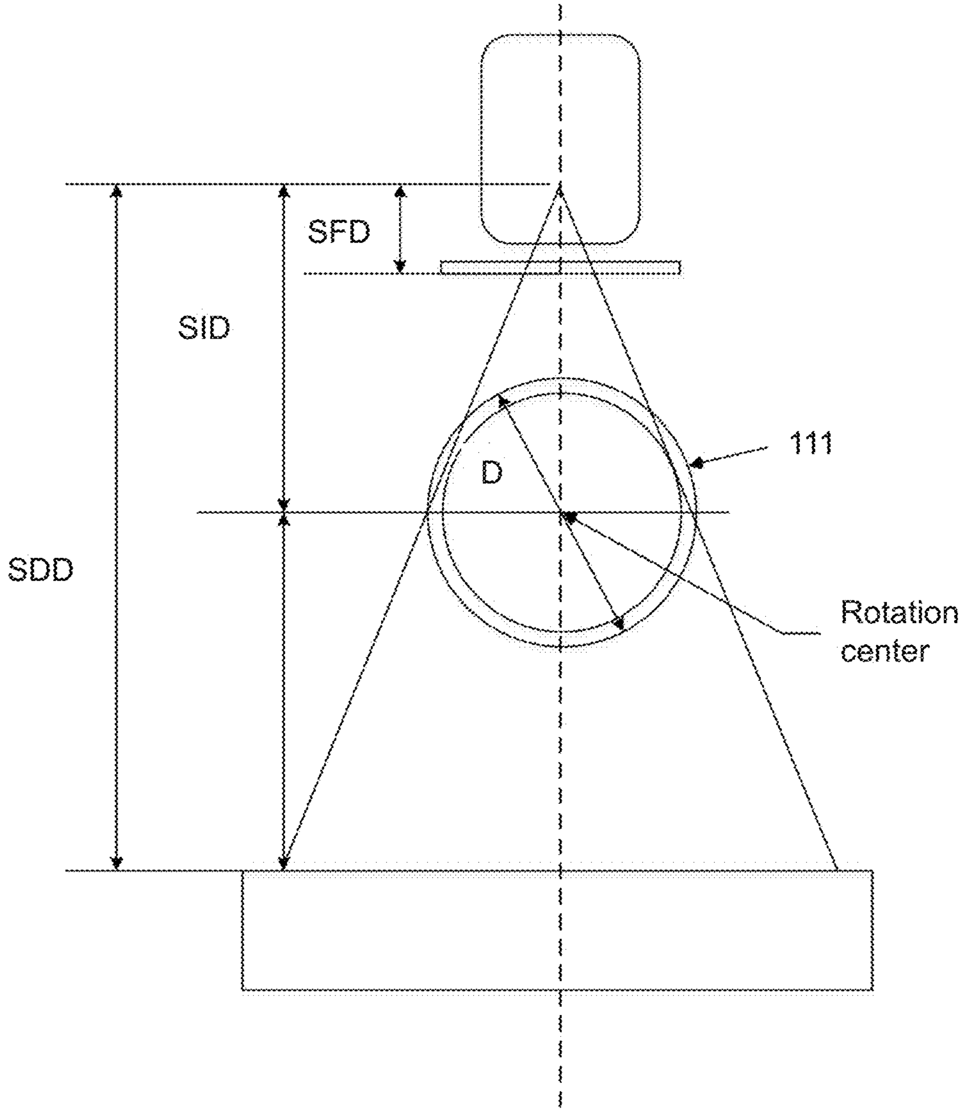
FIG. 7 is a schematic diagram illustrating an exemplary geometric configuration of an imaging device according to some embodiments of the present disclosure.

FIG. 7 is a schematic diagram illustrating an exemplary geometric configuration of an imaging device according to some embodiments of the present disclosure. As shown in FIG. 7, a first distance from an X-ray emission window to a detector is denoted as SDD, a second distance from the X-ray emission window to a filter is denoted as SFD, a third distance from the X-ray emission window to a rotation center of a scanning cabin is denoted as SID, an outer diameter of the scanning cabin is denoted as D, and a pixel size of the detector is denoted as dpixelSize. A resolution M and the first distance, the second distance, and the detector pixel size may satisfy a relationship expressed as:

$$M = \frac{(dpixelSize \times SID)}{SDD}$$

wherein, the pixel size of the detector (denoted as dpixelSize) is a fixed parameter of the detector, the first distance SDD is a fixed value. When the resolution of the imaging device (or imaging system) reaches a resolution threshold, the second distance SFD, the third distance SID, and the outer diameter of the scanning cabin D satisfy a geometric condition denoted as:

$$SID = SFD + D/2$$

If the geometric condition is satisfied, the scanning cabin may be at a critical point in contact with the filter, the resolution of the imaging system may reach the resolution threshold, i.e., a minimum value that the resolution may achieve, and the resolution threshold $M_{isotropic}$ may be denoted as:

$$M_{Isotropic} = \frac{\left(dpixelSize \times \left(SFD + \frac{D}{2}\right)\right)}{SDD}$$

The numerical value of the resolution during scanning by the imaging system should satisfy a relation denoted as:

$$Mt \geq M_{Isotropic}$$

Wherein Mt denotes the numerical value of the resolution that may be set during the scanning process. It may be understood that as the third distance SID decreases, more radiation particles are received by an animal scanning slice, resulting in higher resolution in a scanning image, and thus a smaller corresponding numerical value for the resolution. When the scanning cabin is at the critical point in contact with the filter, a distance from the scanning slice to the X-ray emission window reaches the minimum value of SFD+D/2, and at this point, the numerical value of the resolution reaches its minimum value, $M_{isotropic}$. When the scanning cabin is at the critical point in contact with the detector, the distance from the scanning slice to the X-ray emission window reaches the maximum value of the first distance SDD, and at this point, the numerical value of the resolution reaches its maximum. During the scanning process, if the numerical value of the resolution inputted through the terminal is smaller than $M_{isotropic}$, i.e., the resolution inputted through the terminal exceeds the highest resolution, the imaging system may prohibit SID adjustment to avoid collision between the scanning cabin and the filter, thereby achieving active collision prevention of the imaging system and ensuring system safety. In some embodiments, by determining the resolution threshold of the imaging system, the value range of the resolution of the imaging system can be limited. The value range of the resolution inputted through the terminal may be set based on the resolution threshold determined based on the outer diameter of the scanning cabin, ensuring that value range of the resolution input through the terminal is not less than the resolution threshold.

In some embodiments of the present disclosure, the resolution inputted through the terminal is obtained and whether the numerical value of the resolution is less than the resolution threshold is determined. In response to a determination that the resolution is less than the resolution threshold, the prompt message is outputted to suggest re-entering the resolution or replacing the scanning cabin. By comparing the resolution with the resolution threshold to avoid system safety accidents and outputting the prompt message, the safety of the imaging system can be enhanced.

More descriptions of the imaging device in the imaging system of the embodiments of the present disclosure may be described in conjunction with the accompanying drawings.

Figure 8:
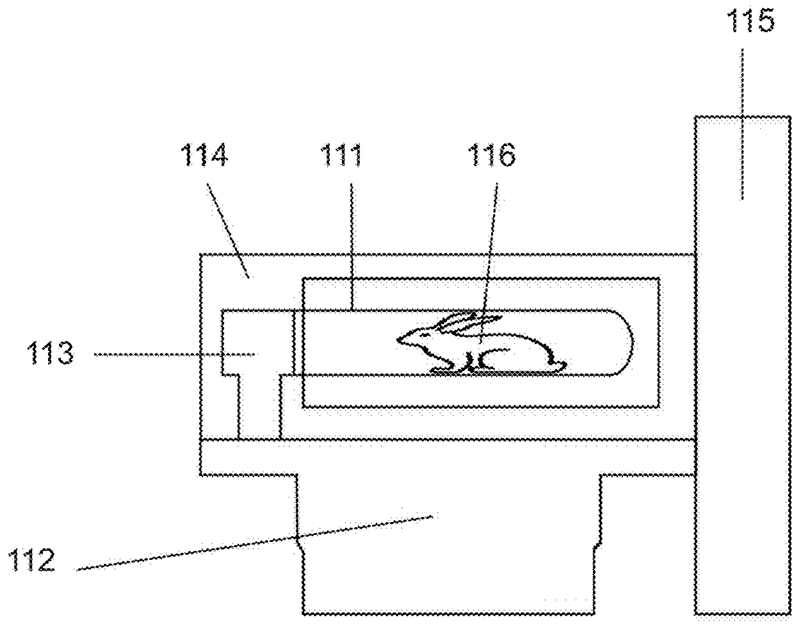
FIG. 8 is a schematic diagram illustrating an exemplary structure of an imaging device according to some embodiments of the present disclosure.
Figure 9:
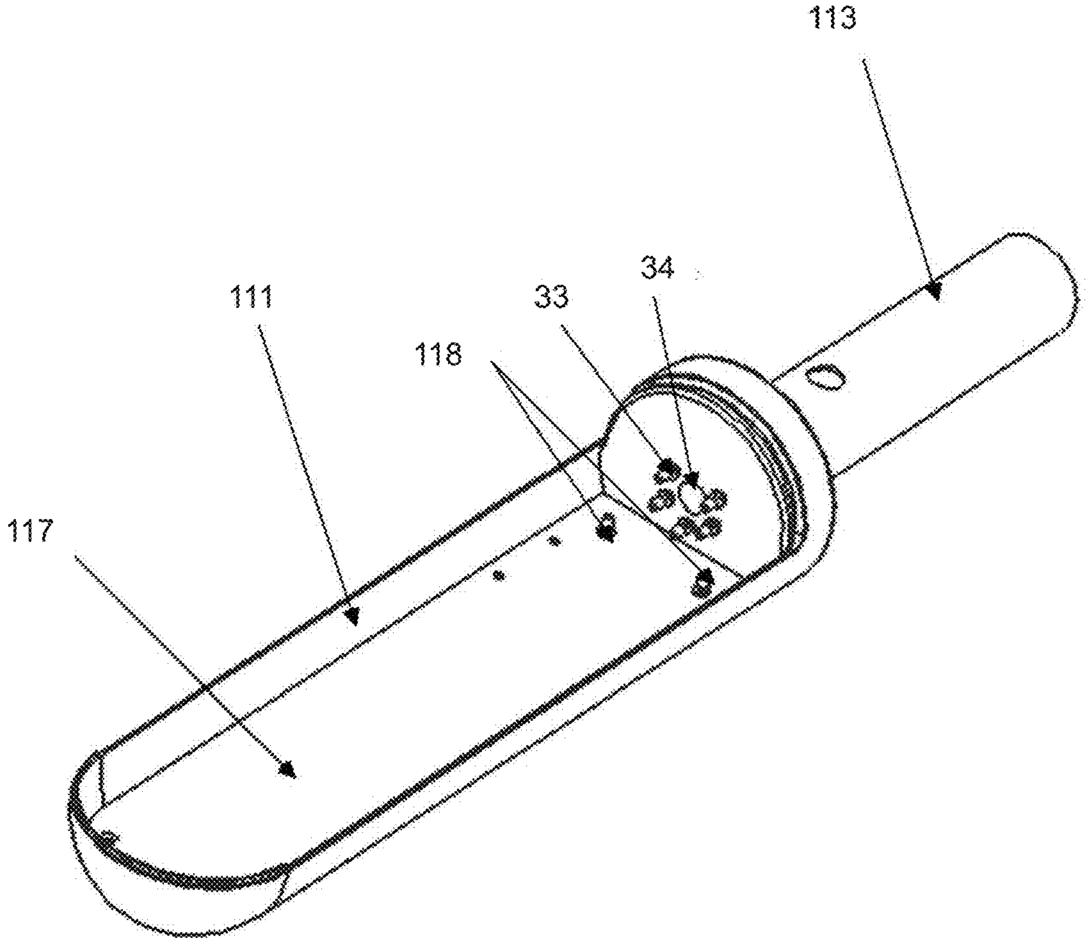
FIG. 9 is a schematic diagram illustrating an exemplary structure of a scanning cabin and a scanning cabin support arm according to some embodiments of the present disclosure.
Figure 10:
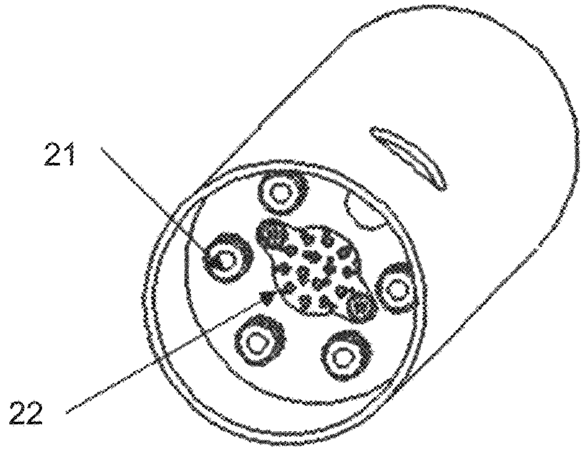
FIG. 10 is a schematic diagram illustrating an exemplary structure of a scanning cabin support arm according to some embodiments of the present disclosure.
Figure 11:
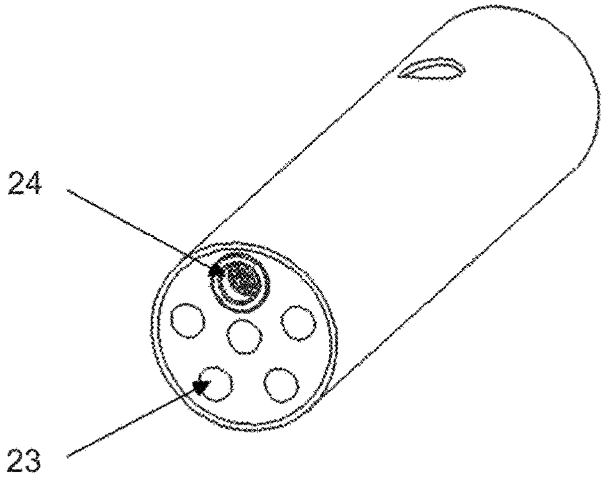
FIG. 11 is a schematic diagram illustrating an exemplary structure of a scanning cabin support arm according to some embodiments of the present disclosure.
Figure 12:
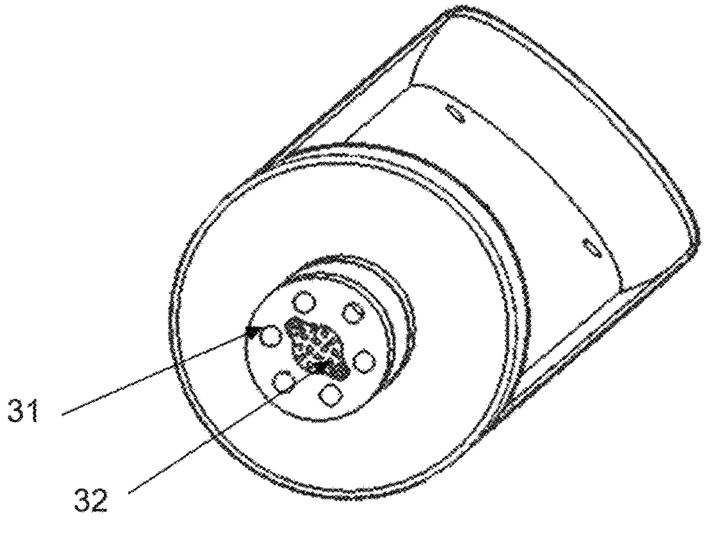
FIG. 12 is a schematic diagram illustrating an exemplary structure of a scanning cabin according to some embodiments of the present disclosure.

FIG. 8 is a schematic diagram illustrating an exemplary structure of an imaging device according to some embodiments of the present disclosure. FIG. 9 is a schematic diagram illustrating an exemplary structure of a scanning cabin and a scanning cabin support arm according to some embodiments of the present disclosure. FIGS. 10-11 are schematic diagrams illustrating exemplary structures of scanning cabin support arms according to some embodiments of the present disclosure. FIG. 12 is a schematic diagram illustrating an exemplary structure of a scanning cabin according to some embodiments of the present disclosure. Specifically, as shown in FIG. 8, an imaging device 110 may include a scanning cabin 111, a scanning bed 112, a scanning cabin support arm 113, a cabin cover 114, a scanning device 115, and a scanning object 116. The scanning bed 112 has a feed mechanism that may drive the scanning cabin 113 to feed axially along an X direction shown in FIG. 8. The scanning cabin support arm 113 is fixed on the feed mechanism of the scanning bed 112, and a connector plug on the scanning cabin support arm 113 may be connected with a connector socket on the scanning cabin 111, forming a replaceable quick-release connection structure between the scanning cabin support arm 113 and the scanning cabin 111, which may be quickly plugged and unplugged, facilitating the selection of the appropriate scanning cabin 111 according to different scanning objects 116. The scanning object 116 is located inside the scanning cabin 111, and is fed into the scanning device 115 for imaging through the feed mechanism of the scanning bed 112, obtaining a scanning image such as a CT image, a PET image, a SPECT image, and a combination image of different modalities.

In some embodiments, as shown in FIGS. 8-12, an integral structure formed by the scanning cabin 111 and the scanning cabin support arm 113 may include the scanning cabin support arm 113, the scanning cabin 111, a partition 117, and a hot air interface 118. A first gas and gas signal transmission pipeline 21, an electrical signal transmission connector plug 22, an external gas and gas signal connector 23, and an external signal connector 24 are fixed on the scanning cabin support arm 113. A second gas and gas signal transmission pipeline 31, an electrical signal transmission connector socket 32, an internal gas and gas signal connector 33, and an internal signal connector 34 are fixed on the scanning cabin 111. Furthermore, the first gas and gas signal transmission pipeline 21 is connected to the second gas and gas signal transmission pipeline 31, and the electrical signal transmission connector plug 22 is connected to the electrical signal transmission connector socket 32. In some embodiments, a space exists between the partition 117 and the scanning cabin 111 and the space is used to receive hot air and control a temperature inside the scanning cabin 111.

In some embodiments, by connecting the electrical signal transmission connector plug 22 and the electrical signal transmission connector socket 32, transmission of an internal signal of the scanning cabin 111 may be realized. In some embodiments, the internal signal in the cabin may include an ECG signal (i.e., electrocardiographic signal) and a temperature signal of a live sample (i.e., the scanning object 116), a specification parameter of the scanning cabin, internal temperature information, or a combination thereof. As an illustrative example, after the ECG signal and the temperature signal of the live sample are collected by sensors in a small animal physiological monitoring unit, the collected ECG signal and temperature signal are transmitted through the electrical signal transmission connector socket 32 and the electrical signal transmission connector plug 22, and finally processed by an external signal processing module through the external signal connector 24.

In some embodiments, by connecting the first gas and gas signal transmission pipeline 21 and the second gas and gas signal transmission pipeline 31, transmission of an internal gas and a gas signal of the scanning cabin 111 may be realized. In some embodiments, the internal gas may include an anesthesia gas and adjustable temperature warm air, and the gas signal may include a respiratory signal. As an illustrative example, the adjustable temperature warm air passes through the first gas and gas signal transmission pipeline 21, the second gas and gas signal transmission pipeline 31, and finally enters the space between the partition 117 and the scanning cabin 111 through the hot air interface 118 to adjust an internal temperature of the scanning cabin, while avoiding direct blowing of the warm air onto the scanning object 116 inside the scanning cabin 111, thus preventing damage to the scanning object 116. The respiratory signal is collected and then transmitted through the internal gas and gas signal connector 33, the second gas and gas signal transmission pipeline 31, the first gas and gas signal transmission pipeline 21, the external gas and gas signal connector 23 successively, and finally sent to the external signal processing module.

In some embodiments, for different scanning cabins with different specification parameters and imaging devices with different scanning parameters, a connection manner (e.g., the wiring manner of the plurality of I/O interfaces) between the connector plug (e.g., the electrical signal transmission connector plug 22) and the connector socket (e.g., the electrical signal transmission connector socket 32) may be used to determine the specification parameter of the corresponding scanning cabin and other signals.

Figure 13:
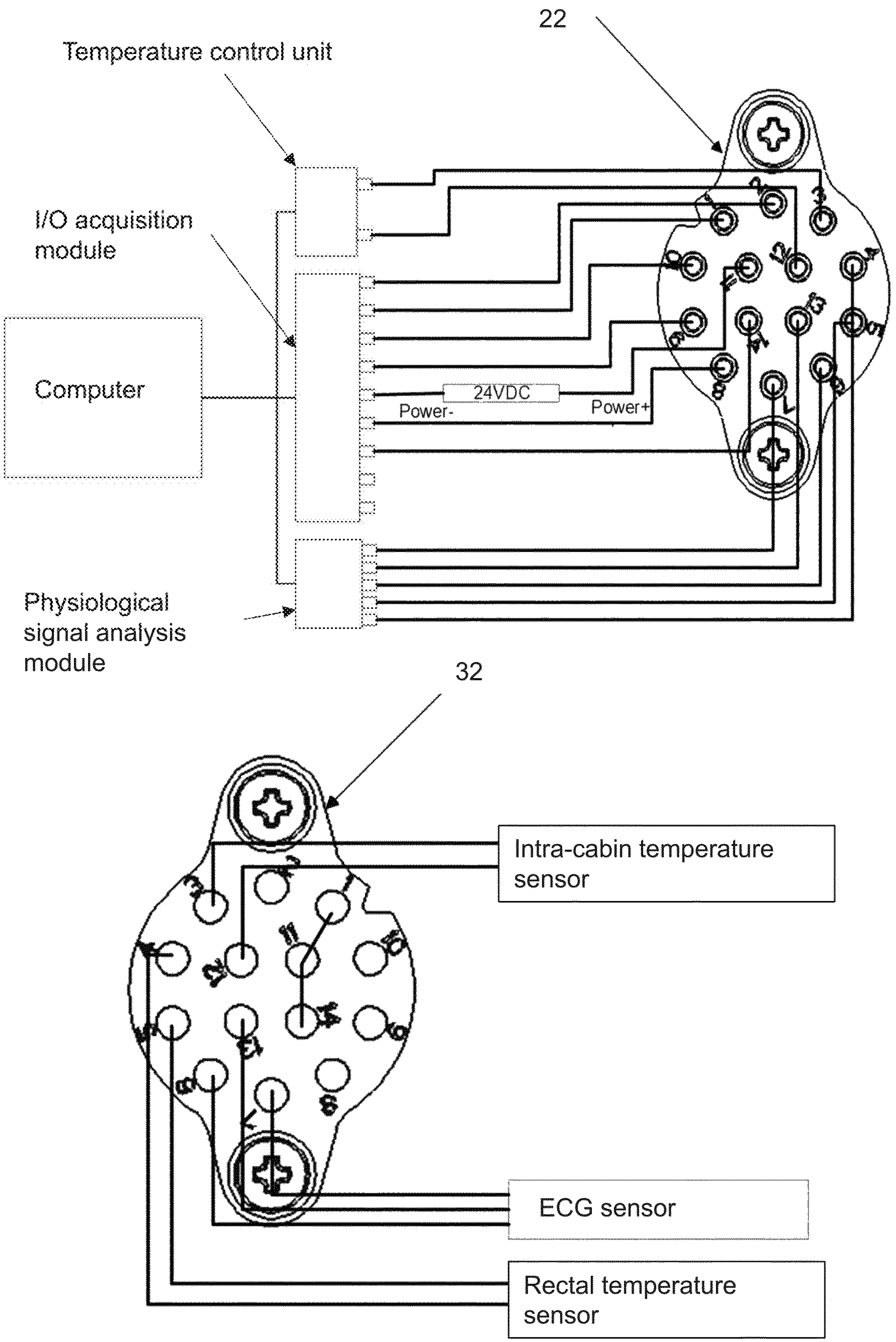
FIG. 13 is a schematic diagram illustrating an exemplary structure of a connector interface according to some embodiments of the present disclosure.

FIG. 13 is a schematic diagram illustrating an exemplary structure of a connector interface according to some embodiments of the present disclosure.

As shown in FIG. 13, the connector interface may include a temperature control unit interface, an I/O acquisition module interface, a physiological signal analysis module interface, an intra-cabin temperature sensor interface, an ECG sensor interface, and a rectal temperature sensor interface. Specifically, a temperature control unit may be configured to control a real-time temperature inside a scanning cabin; an I/O acquisition module may be configured to obtain status values of a plurality of I/O interfaces on a connector socket (e.g., the electrical signal transmission connector socket 32) for transmitting an electrical signal and determine a category (or specification parameter) of the scanning cabin based on the status values (i.e., coding information); a physiological signal analysis module may be configured to transmit and analyze a physiological signal of a scanning object; an intra-cabin temperature sensor may be configured to obtain the real-time temperature inside the scanning cabin and convert it into an electrical signal to be transmitted to the temperature control unit; an ECG sensor may be configured to obtain an ECG signal of the scanning object to assess a health condition of the scanning object; and a rectal temperature sensor may be configured to obtain a rectal temperature of the scanning object for user retrieval. Different interfaces may be selected based on different connection manners to achieve functions such as temperature control, acquisition of the status values of the plurality of I/O interfaces, physiological signal analysis, or the like.

The imaging system provided in some embodiments of the present disclosure achieves accurate identification of the scanning cabin by setting the scanning cabin to be replaceable and then applying the method for identifying the scanning cabin provided in some embodiments of the present disclosure. The method obtains preset information of the scanning cabin and determine the specification parameter and one or more scanning parameters of the scanning cabin based on the preset information and the coding information, thus achieving accurate identification of the scanning cabin, reducing identification costs, and improving identification efficiency.

Additionally, the imaging system provided in some embodiments of the present disclosure may also monitor a physiological status of the scanning object. In some embodiments, the imaging system provided in the present disclosure may monitor the physiological status (e.g., body temperature, respiration, electrocardiogram, etc.) of the scanning object through the scanning cabin. In some embodiments, the monitoring of the physiological status of the scanning object by the scanning cabin may be contact-based physiological monitoring. Specifically, the scanning cabin is provided with a detection device for detecting the physiological status of the scanning object, which needs direct contact with the scanning object to detect the corresponding physiological status signal. The signal is then transmitted via a transmission cable to an exterior of the scanning cabin to achieve physiological monitoring of the scanning object. For example, when monitoring the body temperature of the scanning object, the rectal temperature sensor is inserted into the scanning object's rectum for temperature measurement. As another example, when monitoring the respiration of the scanning object, a respiratory pad is placed on the abdomen of the scanning object, and a movement of the abdomen compresses gas inside the respiratory pad to generate a respiratory signal. As yet another example, when monitoring the electrocardiogram of the scanning object, an electrode needle is pierced subcutaneously into the scanning object or an electrode patch is attached to a skin of the scanning object for electrode signal acquisition. Contact-based physiological monitoring by the scanning cabin typically requires a longer preparation time. During a preparation process, the scanning object, which is under light anesthesia, may awake, thus placing higher demands on a speed of an operator. Moreover, direct contact between the detection device and the scanning object complicates the operation and may affect an anesthesia state of the scanning object. Furthermore, due to the different specification parameters of scanning cabins adapted for different types and sizes of scanning objects, to facilitate the scanning process, the scanning cabin used in the imaging system for animal scanning is replaceable. However, if contact-based physiological monitoring is used, it may require multiple connections of transmission cables for transmitting the physiological status signals, which may lead to signal attenuation during the transmission process, resulting in poor accuracy of signal measurement. Some embodiments of the present disclosure provide a scanning cabin including one or more functional components integrated on a cabin of the scanning cabin. The one or more functional components may include at least an electrocardiogram detection device, a camera device, and a thermometer. The electrocardiogram detection device enables non-contact monitoring of the scanning object's electrocardiogram, the camera device enables non-contact monitoring of the scanning object's respiratory and/or anesthesia status, and the thermometer enables non-contact physiological monitoring of the scanning object's body temperature, thereby reducing preparation time, facilitating operation, and avoiding interference with the scanning object's anesthesia.

More descriptions of the scanning cabin provided in some embodiments of the present disclosure will be further elaborated in conjunction with the accompanying drawings.

Figure 14:
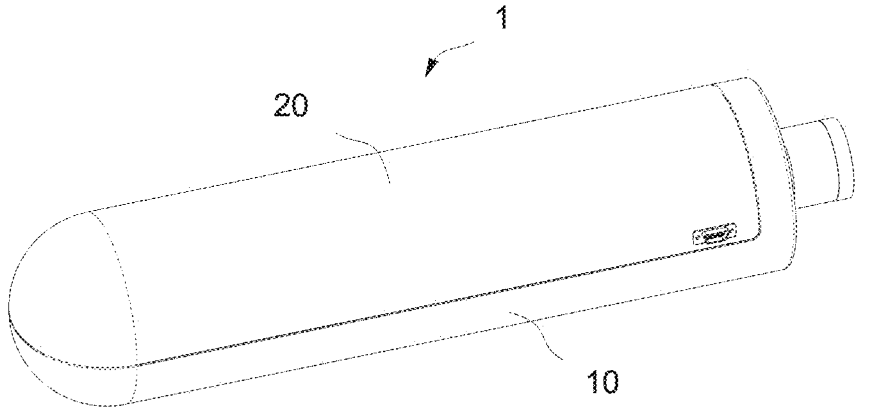
FIG. 14 is a schematic diagram illustrating an exemplary structure of a scanning cabin according to some embodiments of the present disclosure.
Figure 15:
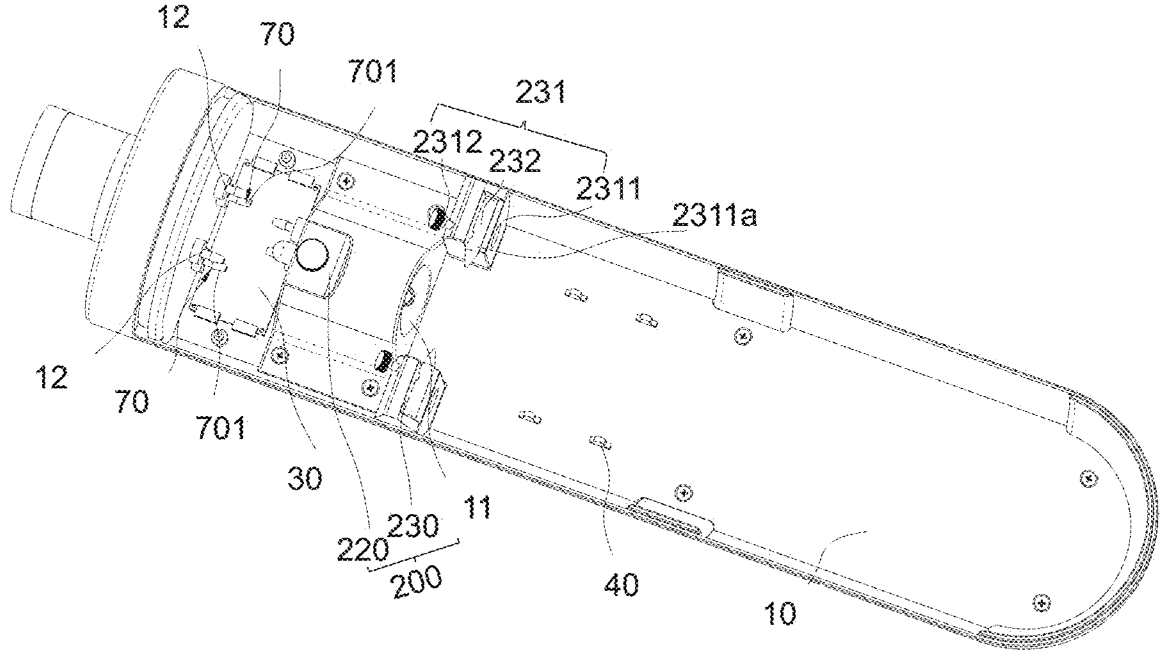
FIG. 15 is a schematic diagram illustrating an exemplary structure of a body of a cabin according to some embodiments of the present disclosure.
Figure 16:
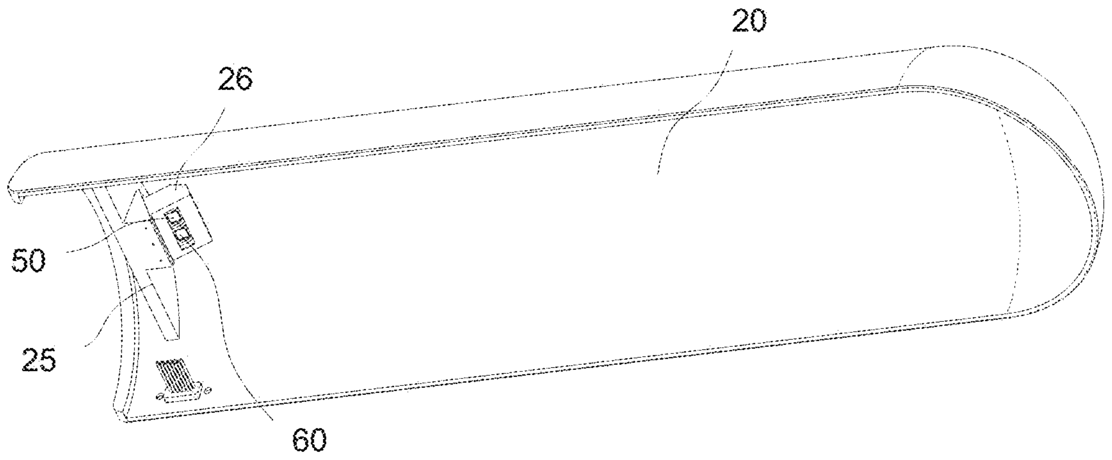
FIG. 16 is a schematic diagram illustrating an exemplary structure of a cabin according to some embodiments of the present disclosure.
Figure 17:
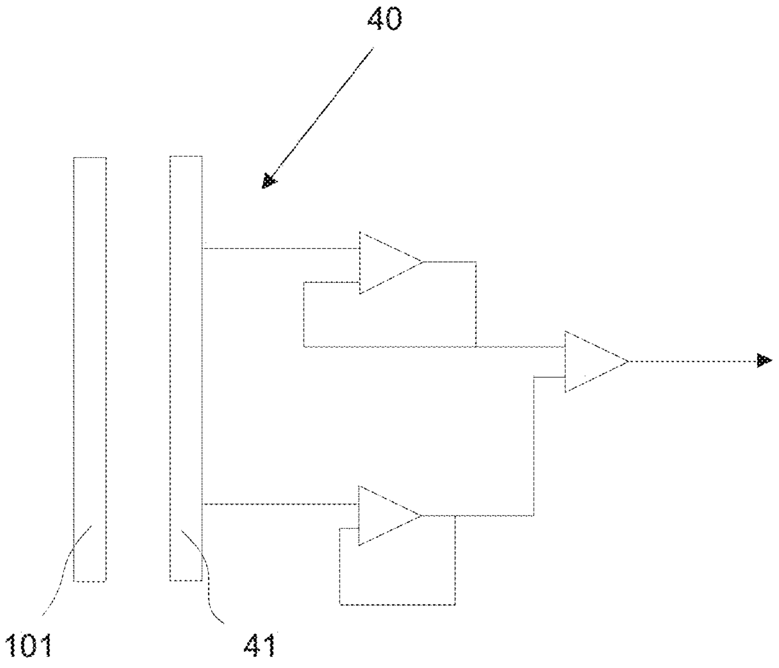
FIG. 17 is a schematic diagram illustrating a working principle of one or more capacitive coupling electrodes detecting electrocardiogram of a scanning object according to some embodiments of the present disclosure.

FIG. 14 is a schematic diagram illustrating an exemplary structure of a scanning cabin according to some embodiments of the present disclosure. FIG. 15 is a schematic diagram illustrating an exemplary structure of a body of a cabin according to some embodiments of the present disclosure. FIG. 16 is a schematic diagram illustrating an exemplary structure of a cabin according to some embodiments of the present disclosure. FIG. 17 is a schematic diagram illustrating a working principle of one or more capacitive coupling electrodes detecting electrocardiogram of a scanning object according to some embodiments of the present disclosure.

As shown in FIG. 14, a scanning cabin 111 may include a cabin 1 for placing a scanning object and one or more functional components (not shown in FIG. 14) integrated in the cabin 1. In some embodiments, the one or more functional components may include an electrocardiogram detection device, a camera device, a thermometer, one or more temperature regulators, a connector socket, a mask, one or more anesthesia circuits, a head fixation assembly, or a combination thereof. The electrocardiogram detection device enables non-contact monitoring of the scanning object's electrocardiogram, the camera device enables non-contact monitoring of the scanning object's respiratory and/or anesthesia status, and the thermometer enables non-contact physiological monitoring of the scanning object's body temperature, thereby reducing preparation time, facilitating operation, and avoiding interference with the scanning object's anesthesia. The connector socket may be configured to transmit information or signals between the scanning cabin and other components (e.g., a terminal, a processing device, etc.) in an imaging system. Specifically, the connector socket may be configured to scan coding information of the scanning cabin into other components of the imaging system for identification of the scanning cabin and to transmit a physiological status signal of the scanning object to other components of the imaging system for analysis based on the physiological status signal of the scanning object to achieve monitoring of a physiological status of the scanning object. The one or more temperature regulators may be configured to adjust a temperature of a region where the scanning object is located to prevent the scanning object from dying due to a decrease in body temperature after entering the anesthesia state. The mask may be configured to cover the mouth of the scanning object to fix the mouth of the scanning object, and the one or more anesthesia circuits may be configured to deliver an anesthetic gas into the mask to anesthetize the scanning object. The head fixation assembly may be configured to fix the ears, teeth, and/or mouth of the scanning object.

In some embodiments, as shown in FIG. 14, the cabin 1 may include a body 10 and a cabin cover 20. The cabin cover 20 may be detachably installed on the body 10 so that during pre-scan preparation of the scanning cabin, the cabin cover 20 may be removed from the body 10 first, then the scanning object may be placed into the body 10, and then the cabin cover 20 may be closed. It may be understood that the integration of the one or more functional components in the cabin 1 does not solely refer to the integration of the one or more functional components on an exterior of the cabin 1 but may also refer to the integration of the one or more functional components inside the cabin 1.

In some embodiments, the one or more functional components integrated in the cabin may be used for electrical connection between the scanning cabin 111 and other components (e.g., the scanning cabin support arm 113 and the processing device 150 shown in FIG. 1) in the imaging system, facilitating the determination of a specification parameter of the scanning cabin 111 and other signals (e.g., physiological signals of the scanning object located inside the scanning cabin 111, including an electrocardiogram signal, a respiration signal, a body temperature signal, an ECG signal, etc.).

In some embodiments, the one or more functional components integrated on the scanning cabin may include the connector socket (e.g., the electrical signal transmission connector socket 32 shown in FIG. 12). The connector socket may be configured to connect with a connector plug (e.g., the electrical signal transmission connector plug 22 shown in FIG. 10) on a scanning cabin support arm (e.g., scanning cabin support arm 113) of the imaging system. After the connection between the connector socket and the connector plug is established, the coding information of the scanning cabin may be generated. Based on the coding information, the specification parameter and/or one or more scanning parameters of the scanning cabin may be identified. More descriptions on identifying the specification parameter and/or the one or more scanning parameters of the scanning cabin based on the coding information may be found in the description of the method for identifying the scanning cabin provided in some embodiments of the present disclosure, which will not be repeated here.

In some embodiments, the cabin 1 is provided with the connector socket that may be connected to the connector plug on the scanning cabin support arm of the imaging system to form a removable quick-connect structure. Specifically, a connector that includes the connector socket and the connector plug may include a POGO connector, wherein the connector plug may be a spring-loaded pin structure, and the connector socket may be a metal contact structure. When the scanning cabin 111 is installed on the scanning cabin support arm, spring-loaded pins of the connector plug press against metal contacts of the connector socket, thus ensuring reliable transmission of electrical signals. It should be understood that the aforementioned POGO connector is provided as an example and is not intended to be limiting. In some embodiments, other types of connectors such as a HDMI interface connector, a USB interface connector, etc., are also within the scope of protection of the connector described in some embodiments of the present disclosure. More descriptions of the connector socket and connector plug may be found elsewhere in the present disclosure (e.g., FIGS. 8-13 and the related descriptions thereof), and will not be repeated here.

In some embodiments, after the connector socket on the scanning cabin 111 is connected to the connector plug on the scanning cabin support arm, coding information of the scanning cabin may be generated. Based on the coding information, the specification parameter and/or the one or more scanning parameters of the scanning cabin 111 may be identified. Specifically, the corresponding coding information may be determined based on the connection manner between the connector plug and the connector socket (e.g., the wiring manner of the plurality of I/O interfaces on the connector socket). More descriptions on how to determine the corresponding coding information based on the connection manner between the connector plug and the connector socket may be found elsewhere in the present disclosure (e.g., FIG. 4 and related descriptions), and will not be repeated here.

The one or more functional components on the scanning cabin in embodiments of the present disclosure include the connector socket, which is configured to connect with the connector plug on the scanning cabin support arm of the imaging system. After the connector socket is connected to the connector plug, the coding information of the scanning cabin may be generated. Based on the coding information, the specification parameter and/or the one or more scanning parameters of the scanning cabin may be identified. By connecting the connector plug with the connector socket, stable and reliable electrical signal transmission is achieved. Moreover, the coding information of the scanning cabin can be directly determined based on the connection manner of the connector socket and the connector plug, eliminating the need for third-party devices to generate the coding information of the scanning cabin, thus improving the efficiency of scanning cabin identification.

In some embodiments, the one or more functional components integrated in the cabin 1 may be configured to monitor physiological data (e.g., electrocardiogram, body temperature, etc.) of the scanning object located inside the scanning cabin 111, and the measured monitoring data may be sent to a control computer (e.g., the controller, the one or more terminals 130, the processing device 140, etc., in the imaging system 100).

In some embodiments, the one or more functional components integrated in the cabin 1 may include an electrocardiogram detection device, which may be configured to perform electrocardiogram detection on the scanning object located inside the cabin 1 to monitor the electrocardiogram of the scanning object. Specifically, the electrocardiogram detection device may be fixed on a body 10 of the cabin 1, allowing the electrocardiogram detection device to be integrated in the cabin 1, thereby enabling non-contact monitoring of the electrocardiogram of the scanning object during an operation (e.g., imaging of the scanning object inside the scanning cabin 111) of the scanning cabin 111. There is no need for electrode needles or electrode patches to come into contact with the scanning object for signal acquisition to monitor the electrocardiogram of the scanning object. This eliminates the need for an operator to pierce electrode needles subcutaneously into the scanning object or attach electrode patches to the skin surface of the scanning object, thus shortening a preparation time, simplifying operation, and not affecting the anesthesia state of the scanning object.

In some embodiments, as shown in FIGS. 15 and 17, the electrocardiogram detection device may include one or more capacitive couplers 40. The one or more capacitive couplers 40 may cooperate with the skin 101 of the limbs of the scanning object and generate a capacitive coupling, thereby specifically realizing a structural arrangement of the electrocardiogram detection device. The structural arrangement of the electrocardiogram detection device allows the scanning cabin 111 to achieve non-contact monitoring of the electrocardiogram of the scanning object by capacitive coupling between the scanning cabin 111 and the skin 101 of the limbs of the scanning object.

In some embodiments, as shown in FIG. 15, a circuit board 30 may be integrated in the cabin 1, and each of the one or more capacitive couplers 40 in the electrocardiogram detection device may be signal-connected to the circuit board 30, respectively. Specifically, each of the one or more capacitive couplers 40 may be signal-connected to the circuit board 30 via a cable and an interface, and each of the one or more capacitive couplers 40 may measure an electrical signal on the skin 101 surface and send the electrical signal to the circuit board 30. It should be noted that the circuit board 30 may include, but is not limited to, a data acquisition module for collecting the electrical signal measured by each of the one or more capacitive couplers 40 on the skin 101 surface. In some embodiments, after receiving the electrical signals transmitted by the one or more capacitive couplers 40, the circuit board 30 may filter, amplify, and discretize the electrical signals, and then transmit the electrical signals to the control computer via a wired or a wireless manner.

In some embodiments, the scanning cabin 111 may achieve non-contact monitoring of the electrocardiogram of the scanning object by capacitive coupling between the one or more capacitive couplers 40 and the skin 101 of the limbs of the scanning object. The capacitive coupling facilitates non-contact monitoring of the electrocardiogram of the scanning object by the scanning cabin 111, which not only reduces the pre-scanning preparation time but also simplifies operation by requiring only the placement of the limbs of the scanning object to the corresponding locations of the one or more capacitive couplers 40, thereby ensuring ease of use without affecting the anesthesia state of the scanning object.

In some embodiments, as shown in FIG. 17, one or more capacitive coupling electrodes 41 are arranged on the one or more capacitive couplers 40. The one or more capacitive coupling electrodes 41 may be configured to form a gap with the skin 101 to allow the one or more capacitive coupling electrodes 41 to generate capacitive coupling with the corresponding skin 101, thus specifically realizing the capacitive coupling generated between the one or more capacitive couplers 40 and the skin 101.

In some embodiments, when the limbs of the scanning object are placed on the one or more capacitive couplers 40, the air between the one or more capacitive coupling electrodes 41 and the corresponding skin 101 and the hair of the scanning object may form a capacitor. The skin 101 and the one or more capacitive coupling electrodes 41 may function as conductors of the capacitor, and the air and the hair of the scanning object may function as insulators. The capacitor may be represented as $C=\pi S/d$, wherein $\pi$ denotes a dielectric constant, S denotes an area of the one or more capacitive coupling electrodes 41, and d denotes a distance between the one or more capacitive coupling electrodes 41 and the skin 101. Therefore, the capacitance value is inversely proportional to the distance between the one or more capacitive coupling electrodes 41 and the skin 101. Furthermore, the electrical signal of the skin 101 of the scanning object may be transmitted to the one or more capacitive coupling electrodes 41 through capacitive coupling, and then transmitted to the circuit board 30 by the one or more capacitive coupling electrodes 41. A differential operation may be performed on the electrical signal to obtain the electrocardiogram signal, thus achieving monitoring of the electrocardiogram of the scanning object.

In some embodiments, a count of the one or more capacitive couplers 40 in the electrocardiogram detection device may be set according to a type, a shape, a size, etc., of the scanning object. In some embodiments, the count of the one or more capacitive couplers 40 in the electrocardiogram detection device may range from 2 to 4. In some embodiments, all of the one or more capacitive couplers 40 in the electrocardiogram detection device may be configured to acquire the electrical signals of the skin of the scanning object. In some embodiments, if the monitoring of the electrocardiogram of the scanning object is achieved based on the electrical signals of the skin obtained through some of the one or more capacitive couplers 40 in the electrocardiogram detection device, the remaining of the one or more capacitive couplers 40 may serve as backups to ensure that monitoring of the scanning object's electrocardiogram may still be achieved in case of failure of some of the one or more capacitive couplers 40 in the electrocardiogram detection device. As an illustrative example, the count of the one or more capacitive couplers 40 in the electrocardiogram detection device may be four, with each of the four capacitive couplers 40 corresponding to one limb of an animal. When the scanning cabin 111 is in operation, monitoring of the animal's electrocardiogram may be achieved by using three of the four capacitive couplers 40 to obtain the electrical signals of the skin, leaving one capacitive coupler 40 as a backup to ensure continuous monitoring of the animal's electrocardiogram.

Additionally, the four capacitive couplers 40 correspond to the four limbs of the scanning object (e.g., a mouse), so that when the scanning object is placed on the body 10 of the cabin 1, each limb of the scanning object may be matched with one of the four capacitive couplers 40. This arrangement enables each of the four capacitive couplers 40 to act on one limb of the scanning object, facilitating the determination of the position of the scanning object in the cabin 1.

In some embodiments, as shown in FIG. 16, the one or more functional components integrated in the cabin 1 may include a camera device 50. The camera device 50 may be configured to capture movements of the abdominal and/or limbs of the scanning object, thereby monitoring a posture and/or a movement status of the scanning object based on the movements of the abdominal and/or limbs. Specifically, the camera device 50 may capture the abdomen and/or limbs of the scanning object in real-time to obtain relevant images of an abdominal movement status and/or a limb movement status of the scanning object. The images may be transmitted to the control computer, which may then monitor a respiratory status and/or an anesthetic status of the scanning object in real-time based on the images of the movements of the abdominal and/or limbs of the scanning object.

In some embodiments, the camera device 50 may function as a respiratory status monitoring device or a part thereof to monitor the respiratory status of the scanning object. Specifically, a respiratory status monitoring device may be arranged in the cabin 1. In some embodiments, the respiratory status monitoring device may adopt a non-contact respiratory status monitoring approach. In some embodiments, the non-contact respiratory status monitoring device may include the camera device 50. The camera device 50 may be fixed on the cabin cover 20 and configured to monitor the respiratory status of the scanning object. When the scanning cabin 111 is in operation, the non-contact monitoring of the respiratory status of the scanning object may be achieved by utilizing a characteristic of the camera device 50. In some embodiments, the non-contact respiratory status monitoring device may include multiple cameras, allowing simultaneous detection of the respiratory status of the scanning object to ensure the accuracy of the respiratory status detected by the non-contact monitoring device. Specifically, the camera device 50 may capture images of the abdomen of the scanning object to monitor the respiratory status of the scanning object based on the movement of the abdomen.

In some embodiments, the camera device 50 may function as an anesthesia status monitoring device or a part thereof to monitor the anesthesia status of the scanning object. In some embodiments, an anesthesia status monitoring device may be integrated in the cabin 1. In some embodiments, the anesthesia status monitoring device may adopt a non-contact anesthesia status monitoring approach. In some embodiments, the non-contact anesthesia status monitoring device may include the camera device 50, which may be fixed on the cabin cover 20 and configured to monitor the anesthesia status of the scanning object. When the scanning cabin 111 is in operation, non-contact monitoring of the anesthesia status of the scanning object may be achieved utilizing the characteristic of the camera device 50. In some embodiments, the non-contact anesthesia status monitoring device includes multiple cameras, enabling simultaneous detection of the animal's anesthesia status to ensure the accuracy of the anesthesia status detected by the non-contact monitoring device. Specifically, the camera device 50 may capture images of the animal's limbs to monitor the anesthesia status based on the movement of the limbs.

In some embodiments, the camera device 50 of the non-contact anesthesia status monitoring device and the non-contact respiratory status monitoring device may include a camera. In some embodiments, the camera device 50 of the non-contact anesthesia status monitoring device and the camera device 50 of the non-contact respiratory status monitoring device may be the same. Specifically, the camera device 50 may capture images of the abdomen of the scanning object to monitor the respiratory status based on the movement of the abdomen; and/or the camera device 50 may capture images of the limbs of the scanning object to monitor the anesthesia status based on the movement of the limbs, thus specifically achieving monitoring of the respiratory and/or anesthesia status of the scanning object when the same camera device 50 is in operation. In some embodiments, the non-contact anesthesia status monitoring device and the non-contact respiratory status monitoring device may use different camera devices to separately monitor the respiratory status and the anesthesia status of the scanning object.

In some embodiments, when the camera device 50 is in operation, the control computer may record a respiratory signal by recording the abdominal movement status of the scanning object. Specifically, measured data may be compared with a normal movement status of the abdomen during the scanning object's normal breathing to determine whether the respiratory status of the scanning object is normal. When monitoring the anesthesia status of the scanning object, specific amplitude values $\lambda$ and $\delta$ for the movement of the limbs of the scanning object may be preset. By comparing a measured amplitude value $\Delta$ of the movement of the limbs of the scanning object monitored by the camera device 50 with the preset amplitude values $\lambda$ and $\delta$, the anesthesia status of the scanning object may be determined. If $\lambda<\delta$ and $\Delta \le \lambda$, it may be determined that the scanning object is in a deep anesthesia state, and the supply of anesthesia gas may be stopped to prevent the scanning object from dying due to excessive anesthesia. If $\lambda < \Delta < \delta$, it may be determined that the scanning object is in a normal anesthesia state, and a supply speed of anesthesia gas may be maintained as needed. If $\Delta \ge \delta$, it may be determined that the scanning object is in a shallow anesthesia or about to wake up, and the supply speed of anesthesia gas may be increased.

In some embodiments, as shown in FIG. 16, the one or more functional components integrated in the cabin 1 may also include a thermometer 60. The thermometer 60 may be non-contact and configured to monitor a temperature of the scanning object without contact, enabling non-contact monitoring of the scanning object's temperature when the scanning cabin 111 is in operation. In some embodiments, the thermometer 60 may be an infrared thermometer and may be fixed on the cabin cover 20.

In some embodiments, one or more temperature regulators 70 may be integrated in the cabin 1. The one or more temperature regulators 70 may be configured to adjust a temperature of a region where the scanning object is located. Specifically, the one or more temperature regulators 70 may be fixed in the body 10 of the cabin 1 and adjust the temperature of the region where the scanning object is located based on temperature data obtained by the thermometer 60, ensuring that the temperature of the scanning object remains normal when the scanning cabin 111 is in operation and preventing the scanning object from experiencing a decrease in temperature and potential death after entering the anesthesia state.

In some embodiments, the one or more temperature regulators 70 may include a heating pipeline 701 that delivers warm air outward. The exchange of warm air with the air inside the body 10 of the cabin 1 and the cabin cover 20 ensures the temperature of the region where the scanning object is located. In some embodiments, the delivery of warm air when the heating pipeline 701 is in operation may be achieved by using an electric heating rod and a fan. Of course, the one or more temperature regulators 70 are not limited to the above description; for those skilled in the art, the one or more temperature regulators 70 may be designed as the electric heating rod directly installed in the body 10, which will not be further elaborated here.

In some embodiments, as shown in FIG. 16, a fixation seat 25 may be arranged on the cabin cover 20 of the cabin 1. The camera device 50 and/or the thermometer 60 may be installed on the fixation seat 25, realizing the installation of the camera device 50 and/or the thermometer 60 on the cabin cover 20.

In some embodiments, as shown in FIG. 16, a shielding box body 26 may be arranged on the cabin cover 20 of the cabin 1, which is configured to shield X-rays. The camera device 50 and/or the thermometer 60 may be installed inside the shielding box body 26 to prevent electronic components within the camera device 50 and/or the thermometer 60 from being damaged by X-rays during the operation of the scanning cabin 111, thereby ensuring that the camera device 50 and/or the thermometer 60 can operate normally without being interfered by X-rays.

In some embodiments, as shown in FIG. 15, the one or more functional components integrated in the cabin 1 may also include a mask 11 and one or more anesthesia circuits 12. The mask 11 may be configured to cover the mouth of the scanning object, and the one or more anesthesia circuits 12 may be configured to connect to the mask 11 to deliver anesthesia gas to the mask 11, achieving anesthesia for the scanning object in the scanning cabin 111. In some embodiments, the mask 11 may be further configured to limit an assembly position of the mouth of the scanning object on the body 10 of the cabin 1. During the operation of the scanning cabin 111, a flow rate of the anesthesia gas delivered to the mask 11 via the one or more anesthesia circuits 12 may be controlled by a flow control valve to coordinate with the monitoring and control of the anesthesia status of the scanning object by the camera device 50, ensuring that the scanning object placed in the body 10 of the cabin 1 remains in the normal anesthesia state.

Figure 18:
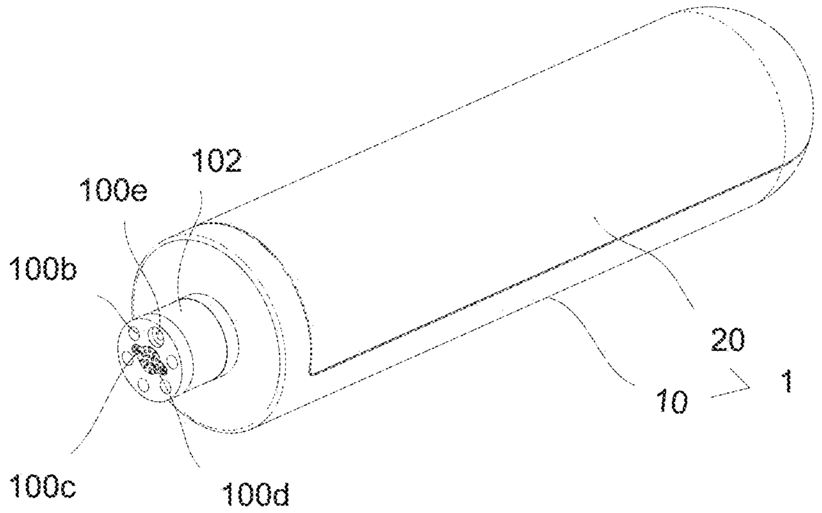
FIG. 18 is a schematic diagram illustrating an exemplary structure of a scanning cabin according to some embodiments of the present disclosure.
Figure 19:
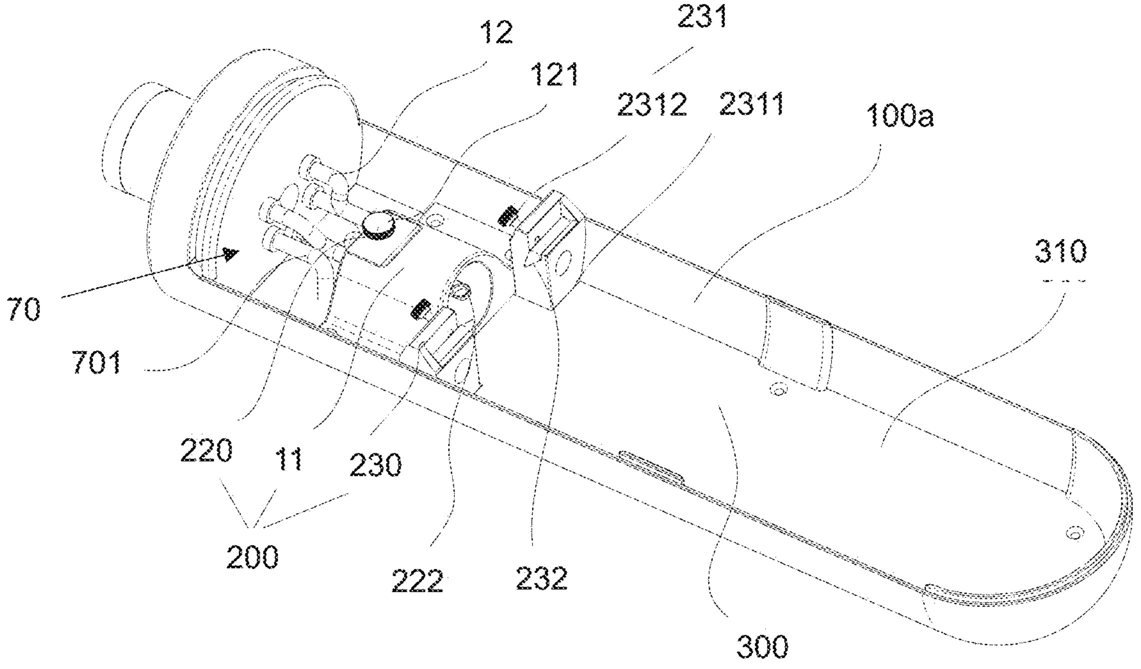
FIG. 19 is a schematic diagram illustrating an exemplary structure of a scanning cabin after removing a cabin cover according to some embodiments of the present disclosure.
Figure 20:
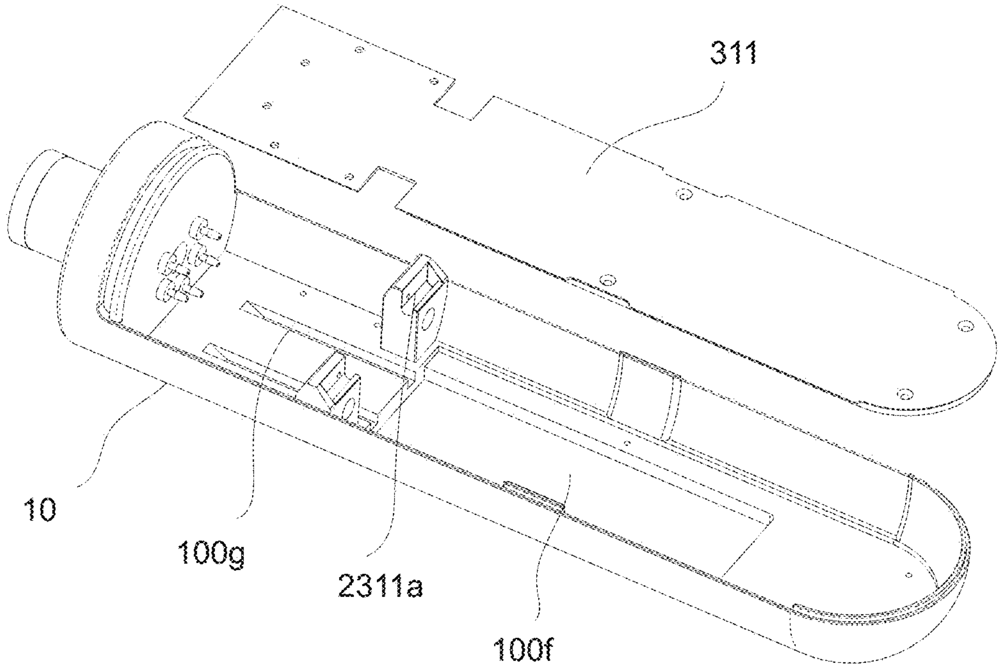
FIG. 20 is a schematic diagram illustrating an exemplary structure of an interior of a cabin according to some embodiments of the present disclosure.
Figure 21:
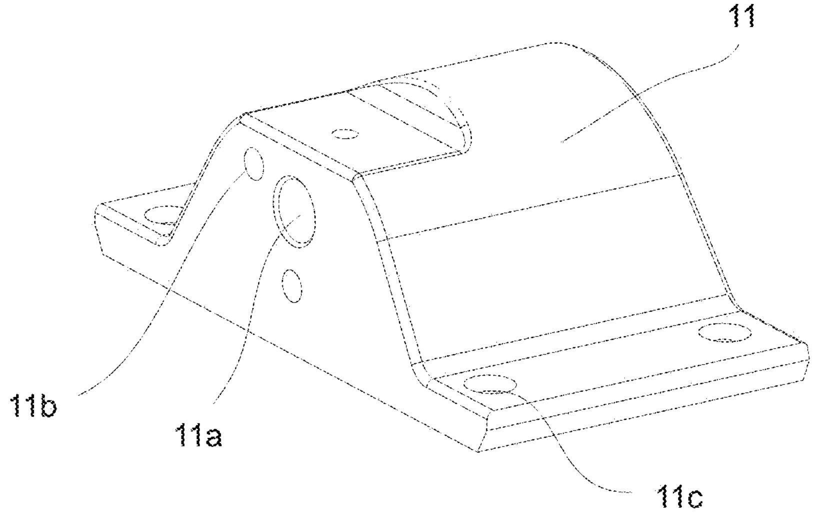
FIG. 21 is a schematic diagram illustrating an exemplary structure of a mask according to some embodiments of the present disclosure.

FIG. 18 is a schematic diagram illustrating an exemplary structure of a scanning cabin according to some embodiments of the present disclosure. FIG. 19 is a schematic diagram illustrating an exemplary structure of a scanning cabin after removing a cabin cover according to some embodiments of the present disclosure. FIG. 20 is a schematic diagram illustrating an exemplary structure of an interior of a cabin according to some embodiments of the present disclosure. FIG. 21 is a schematic diagram illustrating an exemplary structure of a mask according to some embodiments of the present disclosure.

In some embodiments, as shown in FIGS. 18-21, the one or more functional components integrated in the cabin 1 may further include a head fixation assembly 200. The head fixation assembly 200 may be configured to secure the head of a scanning object (e.g., an animal to be scanned) located inside the cabin 1, preventing the scanning object from moving during scanning.

In some embodiments, a cavity 100*a* ma be formed in the interior of the cabin 1 for accommodating the scanning object, and the head fixation assembly 200 may be detachably installed in the cavity 100*a* and configured to secure the head of the scanning object. In some embodiments, the cabin 1 may be provided with one or more pipe joint mounting holes 100*b* and one or more electrical connector mounting holes 100*c* communicating with the interior of the cavity 100*a*. The one or more pipe joint mounting holes 100*b* may be configured to be connected to at least the one or more anesthesia circuits 12 and the heating pipeline 701, and the one or more electrical connector mounting holes 100*c* may be configured to install one or more electrical connectors. In some embodiments, the head fixation assembly 200 may be configured to communicate with the one or more anesthesia circuits 12. Furthermore, the cavity 100*a* may provide a space for placing the scanning object. During a scanning process, the scanning object is placed in the cavity 100*a*, and then the head fixation assembly 200 is configured to secure the head of the scanning object, avoiding inaccuracies in imaging caused by movement of the scanning object during the scanning process. After the head of the scanning object is secured, anesthesia gas is continuously supplied through the one or more anesthesia circuits 12 connected to the one or more pipe joint mounting holes 100*b* to keep the scanning object anesthetized and prevent the scanning object from waking up. During the scanning process, heating gas is continuously introduced into a temperature control component 300 via the heating pipeline 701 connected to the one or more pipe joint mounting holes 100*b*, enabling the temperature control component 300 to heat the scanning object by gas heating, thereby avoiding the need of a power line for electric heating and preventing the power line from affecting imaging. By providing the one or more electrical connector mounting holes 100*c* in the cabin 1, electrical connectors (e.g., a connector socket) may be installed through the one or more electrical connector mounting holes 100*c* to connect various physiological monitoring devices (e.g., a respiratory rate monitoring device, a temperature monitoring device, an electrocardiogram monitoring device, etc.), enabling physiological monitoring of the scanning object and ensuring the stability of a physiological state of the scanning object.

In some embodiments, as the cabin 1 is configured to accommodate the scanning object, so it only needs to have a space for accommodating the scanning object. Specifically, as shown in FIG. 18, the cabin 1 includes the body 10 and the cabin cover 20, and the body 10 and the cabin cover 20 enclose to form the cabin 1 with the cavity 100*a*. By dividing the cabin 1 into the body 10 and the cabin cover 20, it is convenient to disassemble the cabin 1, making it easier to place the scanning object in the cavity 100*a*, and preventing the leakage of anesthesia gas and heating gas. In some embodiments, the body 10 and the cabin cover 20 may be connected through snap-fitting or a threaded connection for easy installation and disassembly. In some embodiments, the cabin cover 20 may slide or flip relative to the body 10 to facilitate opening or closing of the cabin cover 20. For example, a groove may be formed on the body 10, and a part of the cabin cover 20 connected to the body 10 may be located in the groove and may slide within the groove. For example, an edge of the cabin cover 20 and an edge of the body 10 may be connected by a hinge, allowing the cabin cover 20 to flip relative to the body 10. In some embodiments, the head fixation assembly 200 may be disposed in a middle of the body 10 for easy placement of the scanning object. In some embodiments, the head fixation assembly 200 may be disposed at an end of the cavity 100*a* away from a scanning device.

In some embodiments, as shown in FIG. 18, a connecting portion 102 may be formed at a front end of the body 10, which may be configured to connect the cabin 1 with other components (e.g., the scanning cabin support arm 113) in an imaging system. In some embodiments, the connecting portion 102 may include a docking hole 100*e*, through which the cabin 1 may be connected with other components (e.g., the scanning cabin support arm 113) in the imaging system. In some embodiments, the one or more pipe joint mounting holes 100*b* and the one or more electrical connector mounting holes 100*c* may be formed on the connecting portion 102 and extend through the connecting portion 102 into the cavity 100*a*. A count of the one or more pipe joint mounting holes 100*b* is no less than two, with at least one of the one or more pipe joint mounting holes 100*b* for installing the one or more anesthesia circuits 12 and at least one of the one or more pipe joint mounting holes 100*b* for installing the heating pipeline 701. A count of the one or more electrical connector mounting holes 100*c* may be set according to actual needs, which is not limited by embodiments of the present disclosure.

In some embodiments, the cabin cover 20 may be transparent, facilitating the observation of the interior of the cavity 100*a* by an operator.

In some embodiments, to facilitate temperature control of the scanning object, the temperature control component 300 may be placed inside the cavity 100*a*, enabling better heating of the scanning object.

In some embodiments, the cabin 1 may be provided with an electrical connector 100*d* in communication with the cavity 100*a*. The electrical connector 100*d* may be configured to lead various signal lines, further facilitating connections with various physiological monitoring devices. In some embodiments, the electrical connector 100*d* may be the electrical signal transmission connector socket 32 shown in FIG. 9.

In some embodiments, since the mask 11 may be configured to limit the positioning of the mouth of the scanning object in the body 10 of the cabin 1, the mask 11 may be a part of the head fixation assembly 200. The head fixation assembly 200 is configured to secure the head of the scanning object and provide a space for placing the head of the scanning object. In some embodiments, as shown in FIGS. 19 and 21, the head fixation assembly 200 may include the mask 11, a dental fixation mechanism 220, and an ear fixation mechanism 230.

In some embodiments, the mask 11 may be configured to fix the mouth of the scanning object. In some embodiments, the mask 11 may be detachably connected to the cabin 1. Specifically, the mask 11 may be detachably connected to an inner wall of the body 10. A head placement space 11*a* may be formed in the mask 11. The mask 11 may have an opening in communication with a head placement space 210*a* for the head of the scanning object to enter and exit the head placement space 11*a*. In some embodiments, the head placement space 11*a* may be connected to the one or more anesthesia circuits 12 for administering anesthesia to the scanning object.

In some embodiments, as shown in FIG. 21, the mask 11 is provided with a plurality of anesthesia gas inlet and outlet ports 11*b*. The one or more anesthesia circuits 12 may be connected to the head placement space 11*a* through the plurality of anesthesia gas inlet and outlet ports 11*b*, thereby continuously administering anesthesia gas to the scanning object.

In some embodiments, as shown in FIG. 21, a side of the mask 11 is provided with a plurality of bolt holes 11*c*, and the mask 11 is detachably connected to the inner wall of the body 10 through the plurality of bolt holes 11*c*. In some embodiments, a strip groove (not shown in the drawings) may be formed in the body 10. After bolts pass through the plurality of bolt holes 11*c*, the bolts may be located in the strip groove, thereby fixing the mask 11 to the body 10. By changing positions of the plurality of bolt holes 11*c* relative to the strip groove, a fixation position of the mask 11 relative to the body 10 may be adjusted, allowing for adjustable positioning of the head fixation assembly 200 relative to the body 10.

In some embodiments, the dental fixation mechanism 220 may be configured to fix a dental part of the scanning object, thereby preventing the scanning object from moving. In some embodiments, as shown in FIG. 19, to achieve fixation of the dental part of the scanning object, the dental fixation mechanism 220 may include a first fastener 221 and a dental rod 222. The first fastener 221 may be connected to the mask 11 and configured to secure the dental rod 222 inside the head placement space 11*a*. The dental rod 222 may be configured to fix the dental part of the scanning object placed in the head placement space 11*a*. As an illustrative example, when using the dental rod 222, the teeth of the scanning object are bitten into holes on the dental rod 222, thus achieving fixation of the dental part.

In some embodiments, the first fastener 221 may be connected to the dental rod 222. Specifically, the first fastener 221 and the dental rod 222 may be connected via a threaded connection. The first fastener 221 may secure the dental rod 222 inside the head placement space 11*a*. In some embodiments, to simplify a structure of the dental fixation mechanism and facilitate installation, the first fastener 221 may be an adjustable screw. The first fastener 221 may be threadedly connected to the mask 11 and may pass through a top of the mask 11 to secure the dental rod 222, thereby fixing the dental rod 222 inside the head placement space 11*a*. By rotating the first fastener 221, positions of the first fastener 221 may be adjusted, allowing different positions of the first fastener 221 to be connected to the mask 11, thereby enabling the dental rod 222 to be positioned at different locations on the mask 11, thus adjusting a position of the dental rod 222 to accommodate animals of different sizes or types. It should be noted that the first fastener 221 may have other structures, such as directly using a claw to hold the dental rod 222, and adjusting the position of the dental rod 222 by holding the dental rod 222 at different positions. As long as a technical solution can fix the dental rod 222 inside the head placement space 11*a*, the solution is within the scope of protection of the present disclosure.

In some embodiments, the ear fixation mechanism 230 may be configured to fix the ears of the scanning object, thereby achieving fixation of the scanning object. In some embodiments, as shown in FIG. 15 or 19, to achieve fixation of the ears of the scanning object, the ear fixation mechanism 230 may include two relatively arranged ear fixation components, configured to fix the left and right ears of the scanning object, respectively. In some embodiments, the ear fixation component may include a second fastener 231 and two ear rods 232. The second fastener 231 may be disposed on a side of the mask 11 and configured to fix the two ear rods 232. The two ear rods 232 may be configured to fix the ears of the scanning object placed inside the head placement space 11*a*.

In some embodiments, the second fastener 231 may secure the two ear rods 232 at different positions, thereby fixing the ears of scanning objects of different sizes and types. The two ear rods 232 may be configured to fix the left and right ears of the scanning object, respectively. As an illustrative example, when using the two ear rods 232, the two ear rods 232 may be inserted into the left and right ear cavities of the scanning object and pressed against the cavities, thus fixing the ears of the scanning object.

In some embodiments, the second fastener 231 may include a mounting block 2311 and a fastening screw 2312. The mounting block 2311 may be located on a side of the mask 11 and detachably connected to the cabin 1. In some embodiments, the mounting block 2311 may have a mounting groove 2311*a* that coordinates with the ear rod 232, and the fastening screw 2312 may be configured to secure the ear rod 232 inside the mounting groove 2311*a*. During use, the fastening screw 2312 is threadedly connected to the mounting block 2311, passes through a side wall of the mounting block 2311, and abuts against the ear rod 232, allowing the ear rod 232 to be fixed inside the mounting groove 2311*a*, achieving fixation of the ear rod 232. By adjusting a position of the fastening screw 2312 relative to the mounting block 2311, fixation of ear rods 232 of different sizes can be achieved, and a position of the ear rod 232 can be adjusted to enhance adaptability of the ear rod 232. It should be noted that the second fastener 231 may have other structures, such as directly using a claw to hold the ear rod 232, and adjusting the position of the ear rod 232 by holding the ear rod 232 at different positions. As long as a technical solution can fix the ear rod 232, the solution is within the scope of protection of the present disclosure. Additionally, the ear fixation mechanism in the embodiments of the present disclosure is not limited to the ear fixation mechanism 230 shown in FIG. 15 or 19. In some embodiments, the ear fixation mechanism may also use a strap to bind the ears of the scanning object, thereby securing the ears of the scanning object.

In some embodiments, as shown in FIG. 19, the one or more functional components integrated in the cabin 1 may further include the temperature control component 300, which may be configured to achieve gas heating and insulation for the scanning object. The temperature control component 300 may be disposed on a side of the head fixation assembly 200 of the cabin 1. In some embodiments, as shown in FIGS. 19 and 20, the temperature control component 300 includes a heating chamber 310 located inside the cavity 100*a*. The heating chamber 310 may be in communication with the one or more temperature regulators 70. Specifically, the heating chamber 310 may be located at a bottom of the cabin 1 and connected to the heating pipeline 701. By introducing heating gas into the heating chamber 310 through the heating pipeline 701, the heating chamber 310 may be filled with heating gas, thereby achieving heating for the scanning object. In some embodiments, the heating chamber 310 may be arranged separately from the cabin 1 or molded into the cabin 1. In some embodiments, the heating pipeline 701 may be a flexible hose for easy installation.

In some embodiments, as shown in FIG. 20, a groove 100*f* may be formed at the bottom of the cabin 1, and a cover plate 311 may be arranged above the groove 100*f* correspondingly. The cover plate 311 and the groove 100*f* may be enclosed to form the heating chamber 310. By directly creating the groove 100*f* in the cabin 1 and using the cover plate 311 to seal the groove 100*f*, a weight of the entire scanning cabin can be reduced, avoiding the need to separately set up another chamber to achieve heating, making it convenient for molding and installation while enhancing the aesthetic appeal of the entire scanning cabin. In this embodiment, the scanning object is in close contact with the cover plate 311. By adjusting the temperature inside the cavity 100*a*, heating for the scanning object can be achieved, avoiding direct blowing of hot air onto the live scanning object inside the scanning cabin, which may cause damage. In some embodiments, the cover plate 311 may be connected to the groove 100*f* in a detachable manner. A pipe interface in communication with the groove 100*f* may be provided on the cover plate 311. The heating pipeline 701 may be connected to the groove 100*f* through the pipe interface provided on the cover plate 311, eliminating the need to extend the heating pipeline 701 into an interior of the groove 100*f*.

In some embodiments, as shown in FIG. 21, a heating pipeline channel 100*g* may be formed at the bottom of the cabin 1, and the heating pipeline channel 100*g* may extend into the groove 100*f*. The heating pipeline 701 may be arranged inside the heating pipeline channel 100*g*. By providing the heating pipeline channel 100*g*, the installation of the heating pipeline 701 can be facilitated, and the aesthetic appeal of the entire scanning cabin's pipeline layout can be enhanced. In some preferred embodiments, the heating pipeline channel 100*g* may be arranged below the head fixation assembly 200, reducing a length of the heating pipeline channel 100*g*, lowering manufacturing costs, and improving the aesthetic appearance of wiring.

The working principle of the scanning cabin provided in the embodiments of the present disclosure is described below, in conjunction with the scanning cabin shown in FIGS. 18-21.

Before a scanning process, the one or more anesthesia circuits 12 and the heating pipeline 701 are installed through the one or more pipe joint mounting holes 100*b*, and one or more electrical connectors are installed through the one or more electrical connector mounting holes 100*c*. An electrical device is connected via the one or more electrical connectors, and various signal lines are led out through the electrical connector 100*d* into a scanning region inside the cabin 1. Once installation is complete, a scanning object (e.g., an animal) may be placed into the cavity 100*a*. Firstly, the cabin cover 20 may be open, then the head of the scanning object may be placed inside the mask 11, and the head of the scanning object may be fixed using the dental rod 222 and two ear rods 232. Once the scanning process starts, continuous anesthesia of the scanning object is achieved by continuously delivering anesthesia gas into the mask 11 through the one or more anesthesia circuits 12. Simultaneously, heating gas is continuously delivered into the heating chamber 310 through the heating pipeline 701 to maintain the temperature of the scanning object, thereby maintaining the scanning object in a stable state while ensuring fixation, gas anesthesia, heating insulation, and physiological monitoring.

The scanning cabin provided in embodiments of the present disclosure, integrated with the one or more functional components in the cabin, can achieve non-contact monitoring of the scanning object's electrocardiogram, respiratory status, anesthesia status, and body temperature to meet requirements for animal computed tomography imaging. Additionally, during scanning, the scanning cabin in the embodiments of the present disclosure uses the head fixation assembly to fix the head of the scanning object, preventing issues such as inaccurate imaging caused by the movement of the scanning object during scanning. Continuous anesthesia of the scanning object is achieved by delivering anesthesia gas through the one or more anesthesia circuits installed via the one or more pipe joint mounting holes, preventing the scanning object from waking up. Continuous delivery of heating gas into the temperature control component through the heating pipeline installed in the one or more pipe joint mounting holes allows the temperature control component to heat the scanning object through gas heating, avoiding the need for setting up a power supply line for electric heating and preventing the power supply line from affecting imaging. By providing the one or more electrical connector mounting holes and installing one or more electrical connectors, various signal lines are led out through the electrical connectors, facilitating connection with various physiological monitoring devices to ensure the stable physiological status of the scanning object. This simple structure and convenient wiring can improve experimental efficiency.

It is understood that the imaging system provided in the embodiments of the present disclosure includes the scanning cabin described herein. Since the scanning cabin has been described in detail above, the technical effects possessed by the scanning cabin are also possessed by the imaging system, hence they will not be repeated here.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, drawing, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the count of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specification parameters, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present disclosure are not limited to that precisely as shown and described.

What is claimed is:

1. A method implemented on a computing device including a storage device and at least one processor for identifying a scanning cabin, comprising:

obtaining coding information of the scanning cabin;

determining a specification parameter of the scanning cabin based on the coding information and preset coding information; and determining one or more scanning parameters corresponding to the scanning cabin based on the specification parameter of the scanning cabin, wherein the one or more scanning parameters include a resolution threshold corresponding to the scanning cabin.

2. The method of claim 1, wherein the determining a specification parameter of the scanning cabin based on the coding information and preset coding information includes:

determining, from a plurality of pieces of the preset coding information, whether a piece of preset coding information corresponding to the coding information exists in a database, wherein each piece of the plurality of pieces of preset coding information corresponds to a specification parameter of a single scanning cabin;

in response to a determination that the piece of preset coding information corresponding to the coding information exists in the database, obtaining the specification parameter of the scanning cabin corresponding to the piece of preset coding information from the database.

3. The method of claim 2, wherein:

the scanning cabin includes an I/O module;

the I/O module includes a plurality of I/O interfaces; and the coding information of the scanning cabin includes status values of the plurality of I/O interfaces of the I/O module.

4. The method of claim 3, wherein the status values of the plurality of I/O interfaces include a status value of each I/O interface in the plurality of I/O interfaces and a positional sequence of the plurality of I/O interfaces.

5. The method of claim 3, wherein the obtaining coding information of the scanning cabin includes:

obtaining, based on a wiring manner of the plurality of I/O interfaces, the status values of the plurality of I/O interfaces corresponding to the wiring manner.

6. The method of claim 2, wherein before determining whether the piece of preset coding information corresponding to the coding information exists in the database, the method further comprises:

establishing a correspondence between the plurality of pieces of preset coding information and a plurality of specification parameters of a plurality of scanning cabins; and saving the correspondence between the plurality of pieces of preset coding information and the plurality of specification parameters of the plurality of scanning cabins to the database.

7. The method of claim 1, further comprising:

obtaining a resolution inputted through a terminal device, and determining whether the resolution is less than the resolution threshold of the scanning cabin, in response to a determination that the resolution is less than the resolution threshold, providing a prompt message to suggest re-entering the resolution or replacing the scanning cabin; or setting a value range of the resolution inputted through the terminal device based on the resolution threshold.

8. The method of claim 7, wherein the resolution threshold is determined based on a first distance from an X-ray emission window of a scanning device to a detector of the scanning device, a second distance from the X-ray emission window to a filter of the scanning device, an outer diameter of the scanning cabin, and a pixel size of the detector.

9. The method of claim 8, wherein the resolution threshold and the first distance, the second distance, the outer diameter of the scanning cabin, and the pixel size of the detector satisfy a relationship denoted as:

$$M_{Isotropic} = \frac{\left(dpixelSize \times \left(SFD + \frac{D}{2}\right)\right)}{SDD}$$

wherein, $M_{Isotropic}$ denotes the resolution threshold, dpixelSize denotes the pixel size of the detector, SDD denotes the first distance, SFD denotes the second distance, and D denotes the outer diameter of the scanning cabin.

10. A scanning cabin, comprising: a cabin (1) for placing a scanning object and one or more functional components integrated in the cabin, wherein the one or more functional components include:

an electrocardiogram detection device for electrocardiogram detection of the scanning object;

a thermometer (60) for monitoring a body temperature of the scanning object;

one or more temperature regulators (70) for regulating a temperature of a region where the scanning object is located, wherein each of the one or more temperature regulators (70) includes a heating pipeline (701); and a connector socket; wherein the connector socket is configured to connect with a connector plug on a scanning cabin support arm of an imaging system;

the connector socket, when connected with the connector plug, generates coding information of the scanning cabin;

a specification parameter of the scanning cabin are identified based on the coding information; and one or more scanning parameters corresponding to the scanning cabin are determined based on the specification parameter of the scanning cabin and the one or more scanning parameters include a resolution threshold corresponding to the scanning cabin.

11. The scanning cabin of claim 10, wherein the electrocardiogram detection device includes one or more capacitive couplers (40), the capacitive couplers (40) being configured to cooperate with a skin (101) of the scanning object and generate capacitive coupling.

12. The scanning cabin of claim 10, wherein the one or more functional components further include a camera device (50), the camera device (50) being configured to capture the abdomen and/or limbs of the scanning object to obtain an abdominal movement status and/or a limb movement status of the scanning object.

13. The scanning cabin of claim 10, further comprising a head fixation assembly (200) and one or more anesthesia circuits (12), wherein a hollow cavity (100*a*) is formed in an interior of the cabin (1) for accommodating the scanning object; and the head fixation assembly (200) is detachably installed in the cavity (100*a*) and is configured to fix a head of the scanning object.

14. The scanning cabin of claim 13, wherein:

the head fixation assembly (200) includes a mask (11), the mask (11) is configured to cover a mouth of the scanning object, and the one or more anesthesia circuits (12) are in communication with the mask (11) for delivering anesthesia gas to the mask (11).

15. The scanning cabin of claim 14, wherein:

the head fixation assembly (200) includes the mask (11), a dental fixation mechanism (220), and an ear fixation mechanism (230), the mask (11) is detachably connected to the cabin (1), a head placement space (11*a*) is formed in the mask (11), the mask (11) has an opening in communication with the head placement space (11*a*) for the head of the scanning object to enter and exit the head placement space (11*a*), and the head placement space (11*a*) is in communication with the one or more anesthesia circuits (12).

16. The scanning cabin of claim 14, further comprising a temperature control component (300), wherein:

the temperature control component (300) includes a heating chamber (310) located inside the cavity (100*a*), and the heating chamber (310) is in communication with the one or more temperature regulators (70).

17. The scanning cabin of claim 16, wherein:

a groove (100*f*) is formed at a bottom of the cabin (100), a cover plate is provided inside the cavity, and the heating chamber (310) is formed by enclosing the cover plate (311) and the groove (100*f*).

18. The scanning cabin of claim 17, wherein:

a heating pipeline channel (100*g*) is formed at the bottom of the cabin (1), the heating pipeline channel (100*g*) extends into the groove (100*f*), and the heating pipeline (701) is arranged inside the heating pipeline channel (100*g*).

19. An imaging system, comprising a scanning cabin, a scanning cabin support arm, and a controller, wherein:

the scanning cabin includes a connector socket;

a connector plug is provided on the scanning cabin support arm;

the connector socket is configured to connect with the connector plug on the scanning cabin support arm;

the connector socket, when connected with the connector plug, generates coding information for the scanning cabin; and the controller is configured to:

determine whether a piece of preset coding information corresponding to the coding information exists in a database, in response to a determination that the piece of preset coding information corresponding to the coding information exists in the database, obtain a specification parameter of the scanning cabin corresponding to the piece of preset coding information from the database; and determine one or more scanning parameters corresponding to the scanning cabin based on the specification parameter of the scanning cabin, wherein the one or more scanning parameters include a resolution threshold corresponding to the scanning cabin.

20. The imaging system of claim 19, further comprising a scanning device, wherein the scanning device is configured to scan a scanning object inside the scanning cabin to obtain imaging data.

* * * * *